(12) United States Patent
Zhou et al.

(10) Patent No.: US 6,540,951 B1
(45) Date of Patent: Apr. 1, 2003

(54) METHOD FOR REGULATING AGGLOMERATION OF ELASTIC MATERIAL

(75) Inventors: Peiguang Zhou, Appleton, WI (US); Wing-Chak Ng, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 38 days.

(21) Appl. No.: 09/715,808

(22) Filed: Nov. 16, 2000

Related U.S. Application Data
(60) Provisional application No. 60/166,348, filed on Nov. 19, 1999, and provisional application No. 60/222,812, filed on Aug. 4, 2000.

(51) Int. Cl.[7] .......................... B65B 31/00; B65B 51/10; D06M 11/05
(52) U.S. Cl. .......................... 264/340; 53/403; 53/432; 53/477
(58) Field of Search .......................... 264/340; 53/403, 53/432, 477

(56) References Cited

U.S. PATENT DOCUMENTS

| | | |
|---|---|---|
| 3,047,909 A | 8/1962 | Boyer |
| 3,692,618 A | 9/1972 | Dorschner et al. |
| 4,340,563 A | 7/1982 | Appel et al. |
| 4,940,464 A | 7/1990 | Van Gompel et al. |
| 5,536,921 A | 7/1996 | Hedrick et al. |
| 5,902,297 A | 5/1999 | Sauer |
| 5,904,672 A | 5/1999 | LeMahieu et al. |
| 5,904,675 A | 5/1999 | Laux et al. |
| 5,916,203 A | 6/1999 | Brandon et al. |
| 5,964,973 A | 10/1999 | Heath et al. |

FOREIGN PATENT DOCUMENTS

| | | |
|---|---|---|
| EP | 0 935 019 A1 | 8/1999 |
| WO | WO 97/49847 A1 | 12/1997 |

OTHER PUBLICATIONS

W.L. McCabe & J.C. Smith; "Unit Operations of Chemical Engineering"; p. 748; 3rd edition, 1976.
F.W. Billmeyer, Jr.; "Texbook of Polymer Science";pp. 518–530; Wiley–Interscience, Second Edition 1971.
R. Byron Bird et al.; "Transport Phenomena"; pp. 244–247; John Wiley & Sons 1960.
Anonymous; "Globe Manufacturing Corporation Technical Information Bulletin Type S–7 Polyester Spandex Fiber Technology"; pp. 1–24 (undated).
Anonymous; "Dorlastan–Eigenschaften und Einsatzgebiete"; Heinweise fur die Lagerung; p. 7, paragraph 4 (undated).

*Primary Examiner*—Leo B. Tentoni
(74) *Attorney, Agent, or Firm*—Sebastian C. Pugliese, III

(57) ABSTRACT

The present invention is directed to regulating agglomeration of elastic material (e.g., elastic strand) by regulating exposure of the material to water or water vapor. In some versions of the invention, regulating agglomeration in this way decreases, minimizes, or eliminates strand breaks on a production machine using the strand as raw material. Representative embodiments encompass regulating the material's exposure to water or water vapor by regulating temperature, humidity, or both around the elastic material, or containers containing the elastic material, so that the elastic material remains substantially unagglomerated. Other representative embodiments encompass packaging the elastic material in a way that regulates the material's exposure to water or water vapor so that the material remains substantially unagglomerated.

25 Claims, 17 Drawing Sheets

METHOD FOR REGULATING AGGLOMERATION OF ELASTIC MATERIAL

This application claims priority from U.S. Provisional Application Nos. 60/166,348 filed on Nov. 19, 1999 and 60/222,812 filed on Aug. 4, 2000.

BACKGROUND

People rely on disposable absorbent articles to make their lives easier.

Disposable absorbent articles, such as adult incontinence articles and diapers, are generally manufactured by combining several components. These components typically include a liquid-permeable topsheet; a liquid-impermeable backsheet attached to the topsheet; and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Some disposable absorbent articles are constructed with various types of elasticized waistbands and elasticized leg bands or leg cuffs. One method of constructing elasticized regions is to incorporate elastic strands, ribbon, or other material into the disposable absorbent product. For example, elastic strands have been laminated between layers of polymer film and/or layers of woven or nonwoven fabrics to provide such regions. Folded-over layers have also been employed to enclose or envelop selected strands of material. These folded-over layers have been employed to enclose elastomeric strands within the waistband, leg cuff and inner barrier cuff components of disposable diapers and other disposable absorbent articles. The polymeric film or films, layers of woven or nonwoven fabrics, and/or folded-over layers may be an integral portion of the topsheet and/or backsheet discussed above, or may be separate components that are attached to the topsheet and/or backsheet.

In order to introduce an elastic material to the product being made, a spool of the material is generally placed on an unwind stand. For example, a spool of elastic strand on an unwind stand is continuously unwound, in the machine direction, with the strand being attached to a substrate, such as a base layer of material, to provide a substrate composite. As stated above, examples of a base material include, but are not limited to, polymeric films and/or woven or nonwoven fabrics. If a segment of the elastic strand sticks or adheres to a neighboring segment of the elastic strand, then the resulting agglomeration of neighboring segments may be difficult to pull apart when the spool is unwound. In fact, a strand segment may break, leading to costly downtime on a production machine.

What is needed is a method for handling a spool, bobbin, roll, or other container of elastic material so that the material remains substantially unagglomerated; spools, bobbins, rolls, or containers of elastic material in which neighboring segments of the material remain substantially unagglomerated; and substrate composites and absorbent products made using elastic material handled such that the material remains substantially unagglomerated prior to the material's use as a raw material.

SUMMARY

We have determined that neighboring segments of elastic material agglomerate when the material is exposed to water or water vapor. For example, if elastic strand is made at a location different from where the strand is used as a raw material, then the elastic strand must be shipped. During shipping, storage, or other steps the elastic strand may be exposed to amounts of water or water vapor sufficient to cause neighboring segments of the strand to agglomerate. If the strand agglomerates, then it may break more frequently when used as a raw material in a production process (e.g., a conventional, high-speed, disposable-absorbent-article production process running at about 1000 feet per minute or more). Accordingly, the present invention is directed to regulating agglomeration of elastic material by regulating the material's exposure to water or water vapor.

One method having features of the present invention comprises the steps of providing substantially unagglomerated elastic strand; and regulating exposure of the strand to water or water vapor so that the strand remains substantially unagglomerated.

In one representative embodiment, an elastic strand's exposure to water or water vapor is regulated such that the specific humidity around the strand does not exceed about 0.017 pounds-mass of water vapor per pound-mass of dry air, specifically about 0.01 pounds-mass of water vapor per pound-mass of dry air, and more specifically about 0.005 pounds-mass of water vapor per pound-mass of dry air during: storage of the strand at the geographic site where the strand is made, shipping of the strand between the geographic site where the strand is made and the geographic site where the strand is to be used as a raw material, storage of the strand at the geographic site where the strand is to be used as a raw material, or some combination thereof. In some versions of the invention, the strand is used as a raw material to produce a substrate composite comprising the strand or an absorbent article comprising the strand.

Another representative embodiment in which an elastic strand's exposure to water or water vapor is regulated comprises controlling the temperature around the strand or around a container that contains the strand so that the strand remains substantially unagglomerated before the strand's use as a raw material. In one aspect, the temperature is controlled so that it does not exceed about 55 degrees Fahrenheit. By regulating temperature, the maximum humidity that might be attained is regulated (i.e., as air temperature decreases, the capacity of the air to hold water vapor decreases).

In another embodiment, a method in which an elastic strand's exposure to water or water vapor is regulated comprises controlling the humidity around the strand or around a container that contains the strand so that the strand remains substantially unagglomerated before the strand's use as a raw material. In one aspect, the specific humidity is controlled so that it does not exceed about 0.017 pounds-mass of water vapor per pound-mass mass of dry air, specifically about 0.01 pounds-mass of water vapor per pound-mass of dry air, and more specifically about 0.005 pounds-mass of water vapor per pound-mass of dry air.

In some versions of the invention, the elastic strand to which exposure to water or water vapor is regulated comprises polyester, polyurethane, polyether, polyamide, polyacrylate, polyester-b-polyurethane block copolymer, polyether-b-polyurethane block copolymer, or polyether-b-polyamide block copolymer.

Another method having features of the present invention includes the steps of: providing an elastic strand, the elastic strand having been made by steps comprising extruding, spinning, or otherwise making the strand; and regulating the strand's exposure to water vapor so that the Agglomeration Index Value (defined below) does not exceed about 10 grams per strand, particularly does not exceed about 20 grams per strand, more particularly does not exceed about 25 grams per strand, more specifically does not exceed about 30 grams per strand, and suitably is substantially zero at the time it is used as a raw material on a production machine. In another aspect, the production machine is a machine that incorporates one or more elastic strands into a substrate composite or disposable absorbent article.

In another version of the invention, regulation of an elastic strand's exposure to water or water vapor comprises the steps of placing the strand in a container comprising a barrier material resistant to penetration by water vapor, and closing the container so that the strand remains substantially unagglomerated.

In another method of the present invention, the container comprising a barrier material is closed at a time $t_1$, time $t_1$ being after the time when the strand is first produced and before the time when the strand is shipped from the geographical site where the strand is made to the geographical site where the strand is used as a raw material. In another aspect, the specific humidity around the strand does not exceed about 0.017 pounds-mass of water vapor per pound-mass of dry air, specifically about 0.01 pounds-mass of water vapor per pound-mass of dry air, and more specifically about 0.005 pounds-mass of water vapor per pound-mass of dry air between time $t_1$ and time $t_2$, time $t_2$ being the time at which the closed container comprising a barrier material is first opened.

In yet another aspect, the barrier material comprises polyethylene, polypropylene, polyvinyl chloride, polyvinylidene chloride, polyester, polycarbonate, nylon, cellulose, or a combination thereof.

In some versions of the invention, the container comprising barrier material is closed by heat sealing the container, barrier material, or both.

Another method having features of the present invention comprises placing desiccant material with the strand before the container comprising a barrier material is closed (e.g., by heat sealing the barrier material). In another aspect, the desiccant material comprises calcium chloride, calcium sulfate, silica gel, a molecular sieve, $Al_2O_3$, or some combination of thereof.

Other representative embodiments comprise the steps of displacing any mixture of air and water vapor from the interior of the container comprising a barrier material with an inert dry gas before the container is closed (e.g., by heat sealing the barrier material); placing a humidity indicator inside the container comprising a barrier material before the container is closed (e.g., by heat sealing the barrier material); or both.

Still other representative embodiments of the invention include elastic strand handled such that the strand remains substantially unagglomerated by regulating exposure of the strand to water or water vapor, and substrate composites and disposable absorbent products made using such elastic strand.

These and other versions, features, aspects, and advantages of the present invention will become better understood with regard to the following description, appended claims, and accompanying drawings.

DRAWINGS

Figure 12A:
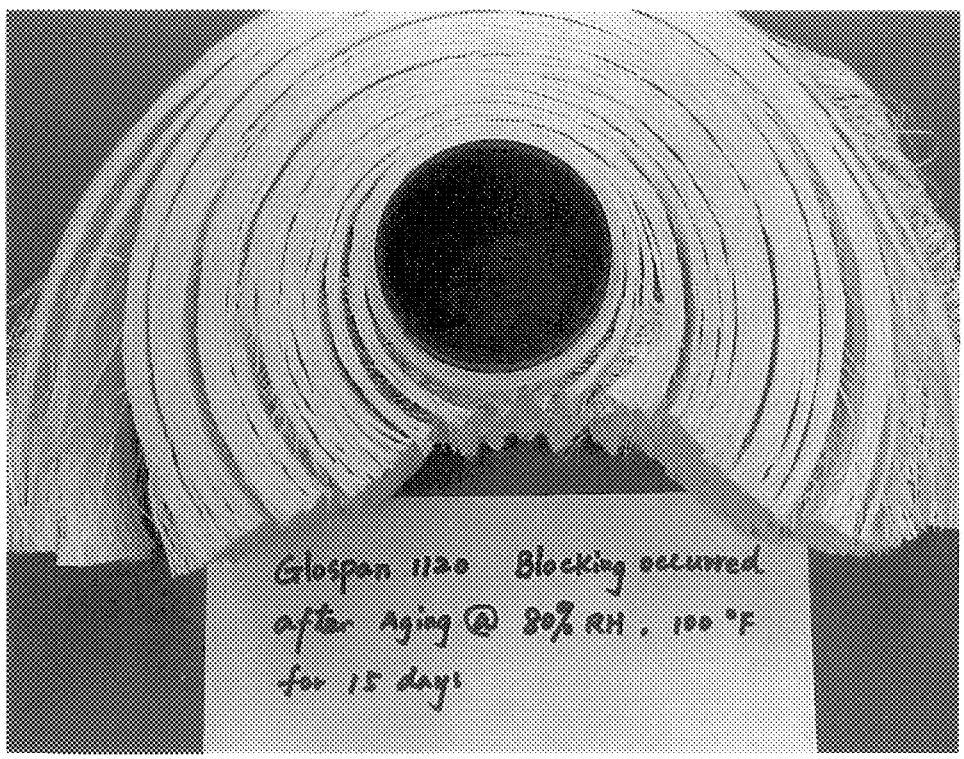
Figure 12B:
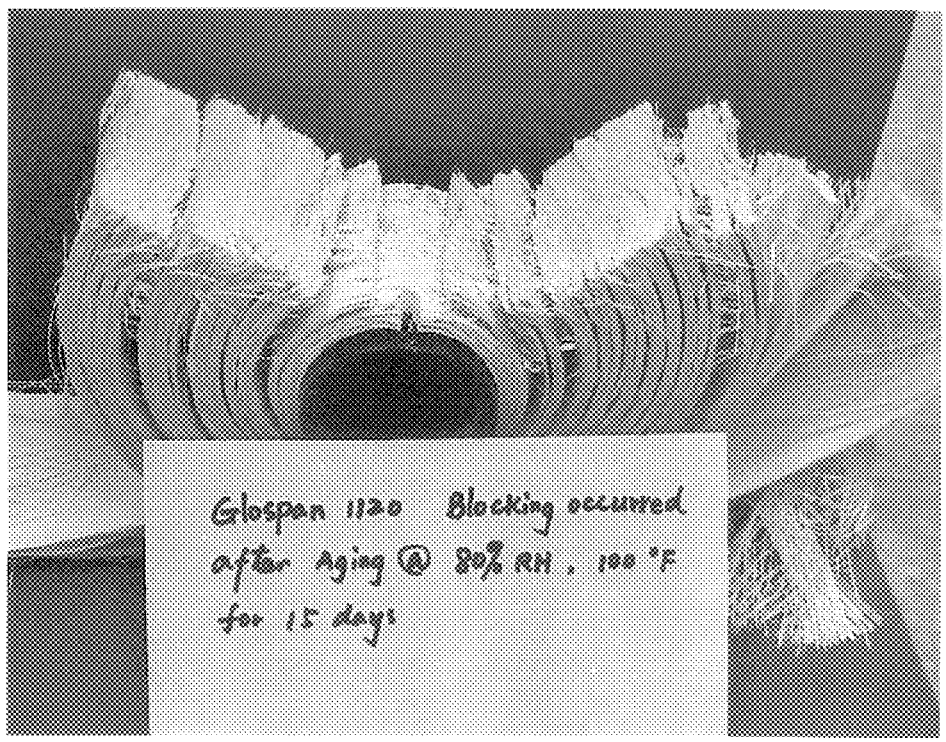
Figure 13A:
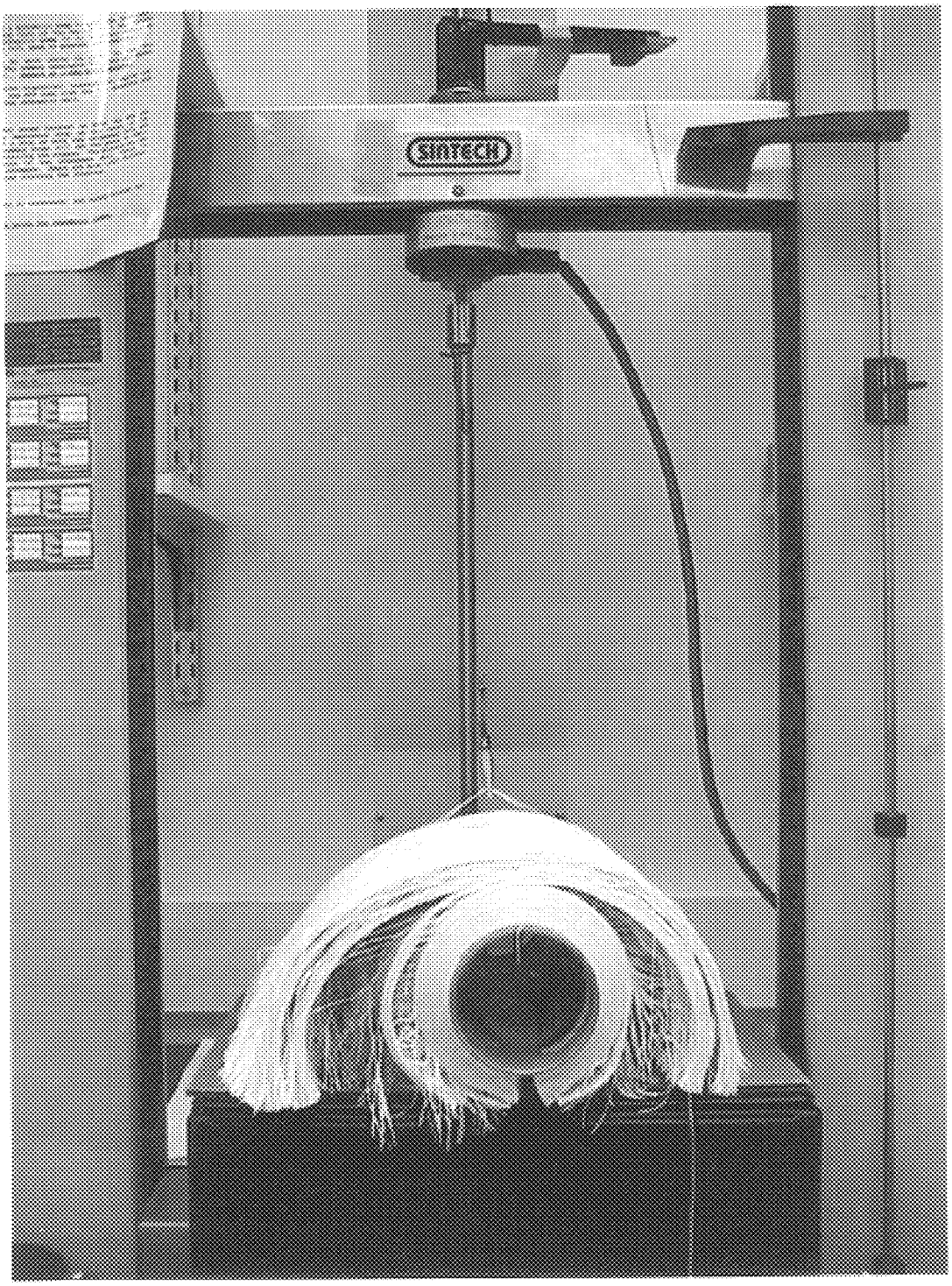
Figure 13B:
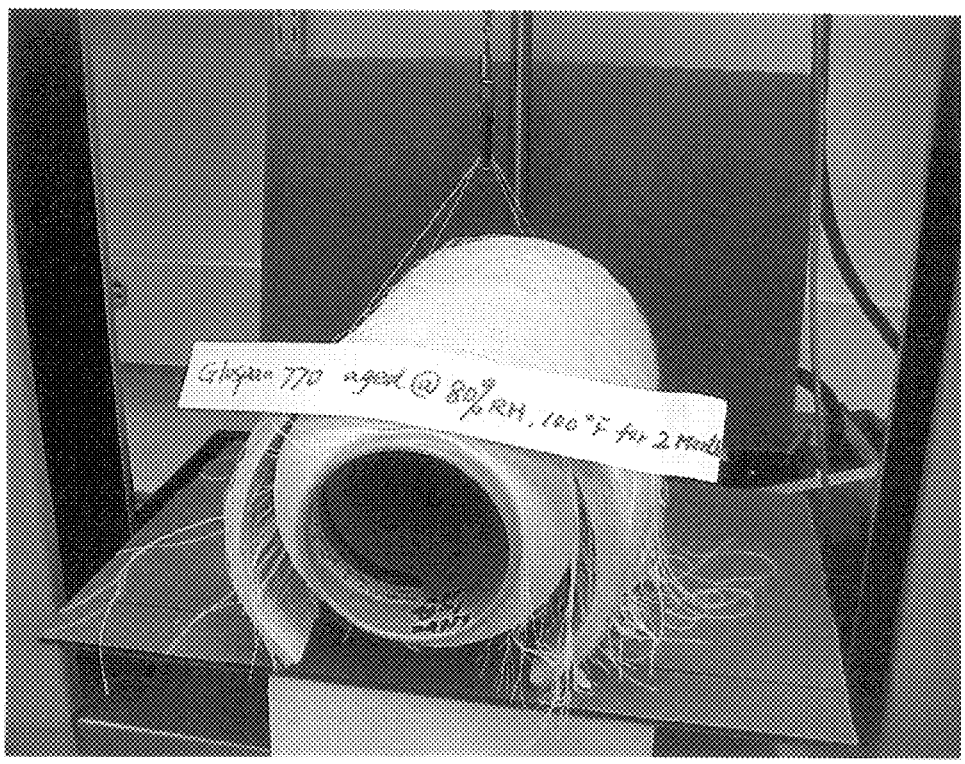
Figure 13C:
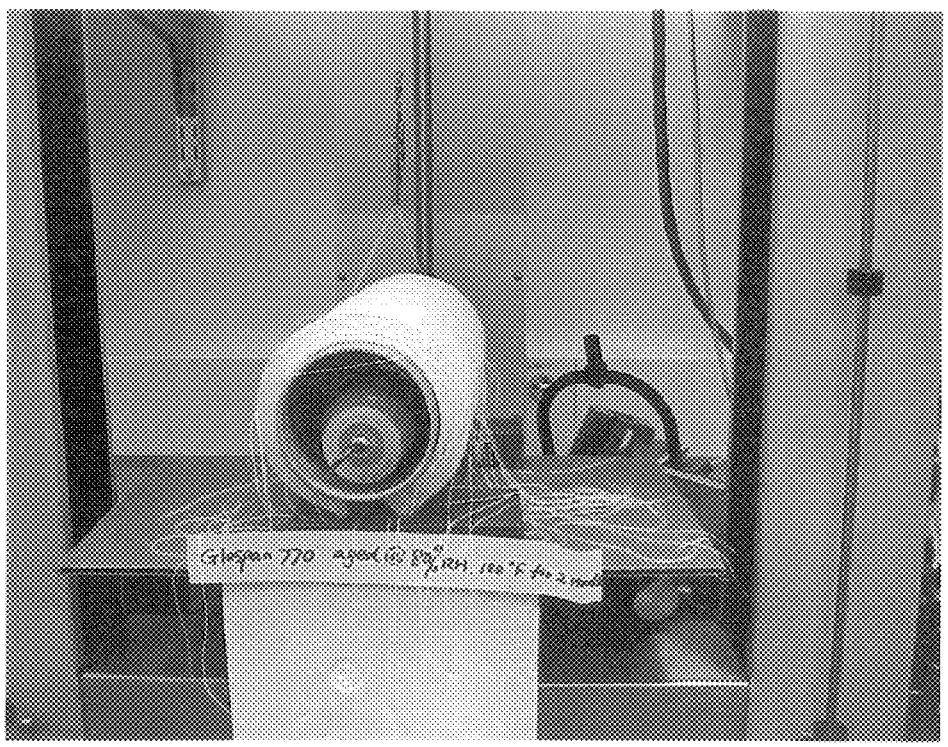
Figure 13D:
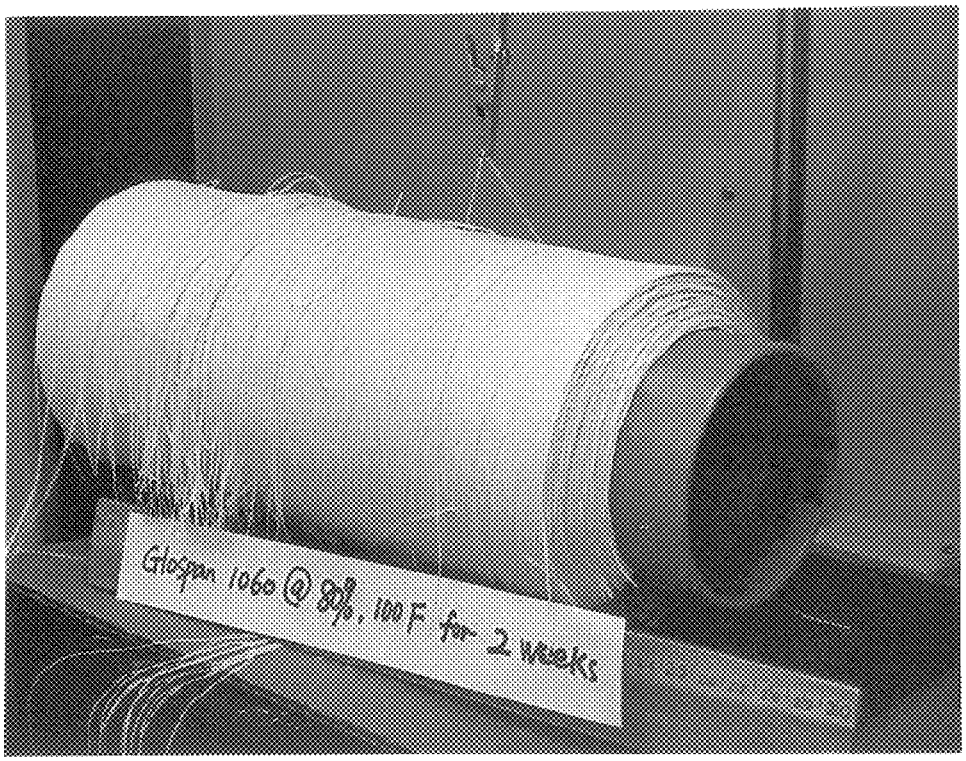

FIGS. 12.A. and 12.B. show images of a slit-open spool of strand (specifically, Glospan 1120, which is available from Globe Manufacturing Company, a business having offices in Fall River, Mass.) after the spool had been exposed to a relative humidity of 80% and a temperature of 100° F. for 15 days.

FIGS. 13.A., 13.B., 13.C., and 13.D show images of a slit-open spool of strand being tested using a tensile-testing device for purposes of determining the Agglomeration Index Value (see below).

DESCRIPTION

The present invention is directed to regulating agglomeration of elastic material by regulating exposure of the material to water or water vapor. In some versions of the invention, regulating agglomeration decreases, minimizes, or eliminates strand breaks on a production machine using the elastic material as a raw material. Several representative embodiments of the present invention are discussed in the following paragraphs.

Figure 1:
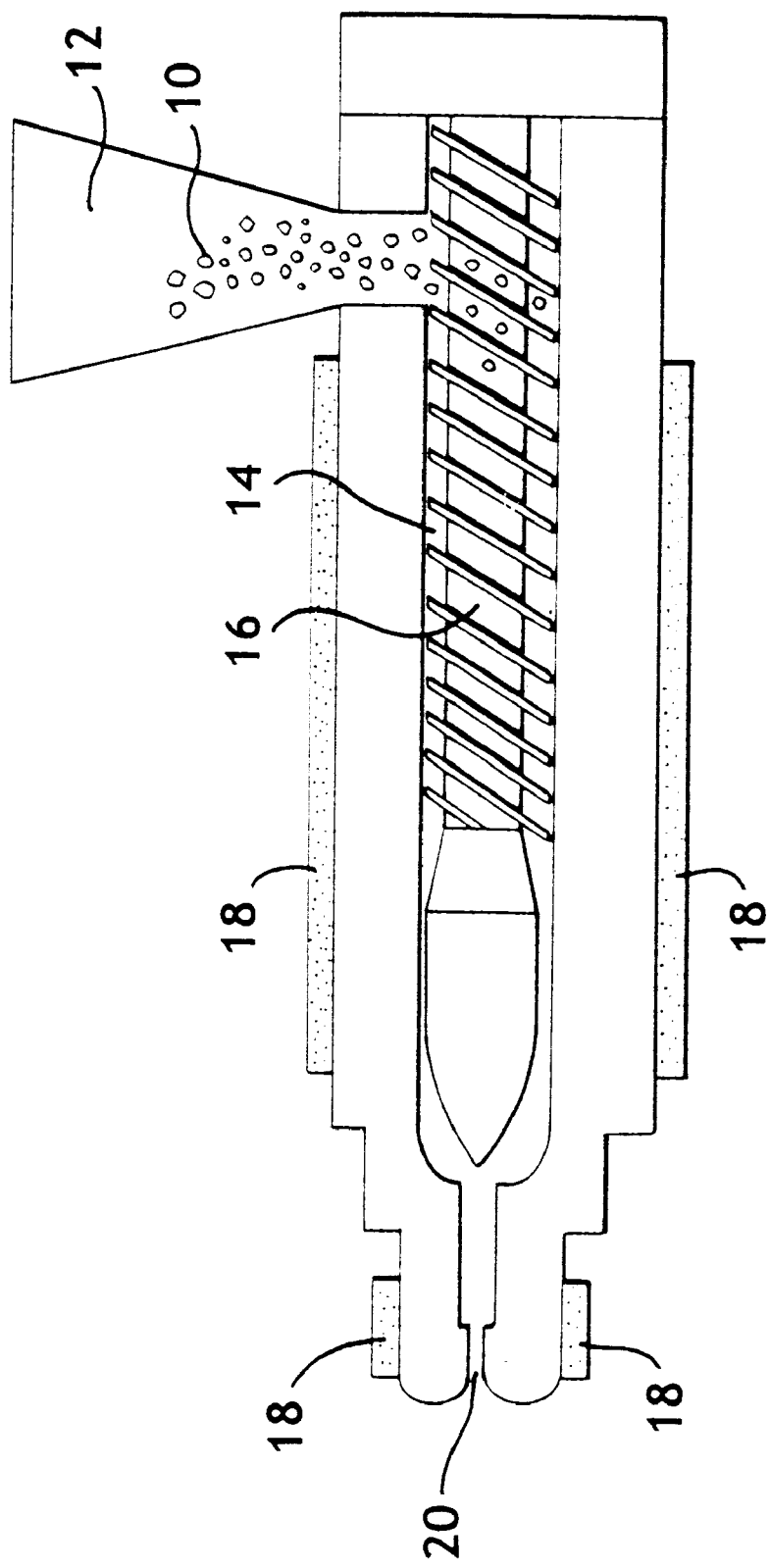
FIG. 1 shows a sectional view of one apparatus for making an elastic strand.

An elastic strand may be made in various ways, including, but not limited to extrusion and spinning. In an extrusion process, depicted in FIG. 1, polymer chips, particulates, pellets, or other solid forms 10 are placed in a hopper 12. The solid polymer is directed from the hopper to a chamber 14. The polymer is propelled continuously through the chamber by a rotating screw 16. As the polymer proceeds through the chamber, the temperature and pressure are such that the solid polymer melts and is compacted. Some of the heat is generated by friction, but typically, an external heating source 18 is also used to heat the polymer. The molten polymer is then forced through a die 20 to give a strand, continuous fiber, ribbon, or filament of a desired structural shape. Possible cross-sectional shapes include, but are not limited to, circular, tri-lobal, polyhedral, rectangular, ribbon-like, or ellipsoidal shapes. Furthermore, the strand may have a variety of cross-sectional dimensions, cross-sectional areas, and/or other physical measurements (e.g., denier or decitex; see Examples below). As discussed below, the present invention covers elastic material that is susceptible to agglomeration due to the action of water or water vapor. The strand cools and solidifies after exiting the extruder.

Rather than use a polymer as a feed material, one or more monomers or pre-polymeric materials may be added to the extruder in chip, particulate, pellet or other solid form. The monomers or pre-polymers may be added with compounds that promote polymerization. Polymerization occurs within the extruder chamber, but may or may not be complete before the material exits through the die. If polymerization is not complete, then some polymerization could occur after the material is extruded. Also, some of the monomer may not ultimately react to become a part of a polymeric chain in the strand.

A number of materials may be extruded to give an elastic strand. The present invention is directed to a strand that is elastic, but is susceptible to attack by water or water vapor (e.g., by a hydrolysis reaction). Examples of materials that can give such an elastic strand include, but are not limited to: polyester, polyurethane; polyether; polyamide; polyacrylate; or combinations thereof, including random, block, or graft copolymers such as polyester-b-polyurethane block copolymers, polyether-b-polyurethane block copolymers, and/or polyether-b-polyamide block copolymers. As stated above, monomeric or pre-polymeric precursors may be added to the extruder to give the polymeric materials of the type just recited.

Crosslinking agents may also be used when making an elastic strand. To the extent that polymeric chains are crosslinked, it is more likely that crosslinking reactions are initiated after the material is extruded. This may be accomplished, for example, in a separate processing step after the strand is extruded.

After the strand exits the extruder, it may be subjected to additional processing steps. These processing steps may take place at some location between extrusion of the strand and the strand being wound up at a bobbin, spindle, or spool for the first time. Alternatively, one or more of these processing steps may take place after the strand has been wound up for the first time. After a bobbin of elastic strand is made, it may later be unwound and treated in some fashion prior to its being wound up again.

Additional processing steps include, but are not limited to, the following. Air might be directed at the strand exiting the die to increase the cooling rate. A scouring step might be included to remove impurities from the strand by exposing the strand to soaps or detergents. A lubricant may be applied to the strand to reduce friction between strands or between the strand and pieces of equipment. Possible lubricants include, but are not limited to, a vegetable or mineral oil, a suitably refined petroleum product, a silicone-based material, or a surfactant. And a drawing step may be included to help orient the polymers to produce desirable physical properties. In one example of a separate drawing step, the strand is directed over two sets of rolls. The strand passes over a first set of rolls moving at a first velocity, then passes over a second set of rolls moving at a second velocity, the second velocity being greater than the first velocity. The difference in velocity between the first and second sets of rolls increases tension on the strand, thereby helping to orient the constituent polymers of the strand, change physical dimensions of the strand, or effect other changes.

After these or other additional processing steps, the strand is wound up for storage or shipment to another geographic location. During this or other steps in which a spool, reel, or bobbin of an elastic strand is unwound and then wound, the strand may be treated with various additives such as cleaning agents, lubricants, or dyes.

In addition to the example of an extrusion process discussed above, various spinning processes may be used to produce an elastic strand or fiber. In general, these processes require dissolving the polymer in solution or melting the polymer.

Figure 2:
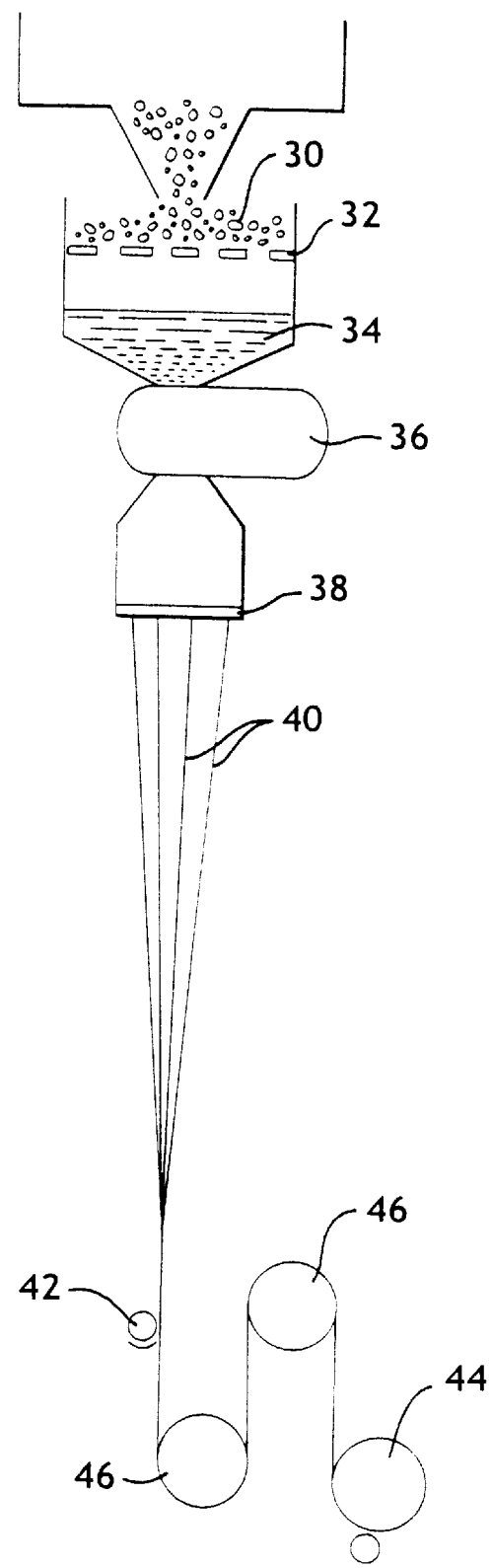
FIG. 2 shows a sectional view of one apparatus for making an elastic strand.

In a melt spinning process, as depicted in FIG. 2, polymer chips, particulates, pellets, or other solid forms 30 are heated by a heated-metal grid 32 or other heating device. The resulting molten polymer 34 is pumped under high pressure through a plate called a spinneret 38. The plate generally defines a plurality of small holes. The molten polymer emerges from the face of the spinneret, usually into air, and solidifies. A number of these strands 40 may be brought together to form a cable- or rope-like structure comprising a plurality of strands.

The polymer typically is melted by contacting a hot grid in the form of steel tubing, which is heated electrically, or by some other means. A metering pump 36, or a combination of a metering pump and a booster pump, may be used to conduct the molten polymer to, and through, the spinneret. Alternatively, an extrusion-type screw may be used to help melt the polymer, and meter the resulting molten polymer, to and through the spinneret.

Generally strands or filaments emerge from the spinneret face into air and begin to cool. Air jets or blasts directed at the emerging strands may be used to speed up the cooling process. After the strands or filaments have traveled far enough to solidify they are processed further. As stated above, additional process steps include, but are not limited to, scouring, lubricating, or drawing the strand or strands. FIG. 2, for example, depicts a lubricating disk and trough 42 for applying a lubricant to one or more strands. After processing is complete the strand—in this case a cable- or rope-like structure—is wound up on a reel, spindle, spool, or bobbin 44 at a winding station. Before being wound up, the strand may pass over one or more rolls 46.

Other spinning processes include wet spinning, in which a solution of a polymer or polymer derivative emerges from a spinneret into a liquid that coagulates the polymer or polymer derivative to form a strand; and dry spinning in which a solution of polymer emerges from the spinneret into air or an inert gas atmosphere into which solvent evaporates, thereby forming a filament or strand.

Generally, the same polymeric or monomeric materials useful for extruding an elastic strand are also useful for spinning an elastic strand. As discussed above, the present invention is directed to a strand that is elastic but is susceptible to attack by water or water vapor. Examples of monomeric or polymeric materials that give such a strand are discussed above. Also, crosslinking agents may be used. Again crosslinking will likely be effected after the strand or filament emerges from the spinneret.

Other descriptions of processes for making strand are given in various publications, e.g. U.S. Pat. Nos. 4,340,563 and 3,692,618, which are hereby incorporated by reference in a manner consistent herewith. It should be understood that the above discussion and referenced publications recite exemplars of ways in which strand is made. The present invention is not limited to these exemplars, but may be used in conjunction with other processes that make an elastic material susceptible to attack by water or water vapor such that neighboring segments of the material stick to or adhere to each other, thus producing agglomeration.

If an elastic strand is made at a geographic location different from the location where the strand is used as a raw material, then the elastic strand must be shipped. Prior to shipment the strand may be stored for some period of time. And the strand may be stored for some period of time after delivery but prior to use as a raw material. Even if the elastic strand is made at the same place where the strand is used as a raw material, the strand may be stored for some time. Depending on the time of year; the location of the site where the strand is made; the location of the site where the strand is used as a raw material; the method of shipment; the time that elapses between spinning, extruding, or otherwise making the strand and utilization of the strand as a raw material, as well as other factors, the elastic strand may be exposed to water or water vapor sufficient to produce agglomeration.

Before referring to figures demonstrating that water vapor may cause a segment of elastic material to attach, stick, or adhere to one or more neighboring segments of elastic material, it is advantageous to discuss certain terms. As discussed herein, "peak load" or "peak-load value" refers to either: (a) the load, measured in grams, placed on a strand segment when the strand segment is pulled from a spool of elastic strand that has been slit lengthwise (discussed below in the section entitled Agglomeration Index Value); or (b) the tensile load, measured in grams, placed on the strand when the strand breaks or fails (discussed below and in co-pending U.S. patent application Ser. No. 60/166348, which the present non-provisional application claims priority from and incorporates by reference in a manner consistent herewith). It should be understood that other measures may be used to characterize the effect of water or water vapor on the tendency of neighboring segments of elastic strand to agglomerate, or the strength characteristics of a strand. As discussed herein, "elongation" refers to the change in length per unit length at peak load. Typically, elongation is recited as a percentage. The term specific humidity generally refers to the mass of vapor carried by a unit mass of vapor-free gas. As used herein, "specific humidity" refers to the mass of water vapor carried by a unit mass of vapor-free gas, the gas typically being air. The term relative humidity generally refers to the ratio of the partial pressure of the vapor to the vapor pressure of the liquid at the gas temperature. It is usually expressed on a percentage basis, so 100 percent relative humidity means that the gas is saturated with vapor and 0 percent relative humidity means that the gas is vapor free. As used herein, "relative humidity" refers to the ratio of the partial pressure of water vapor to the vapor pressure of water at the gas temperature, the gas typically being air. For purposes of this document, "humidity" refers to a measure of the amount of water vapor in a gas, typically air, and unless stated otherwise, refers to specific humidity and/or relative humidity. The term dew point generally refers to the temperature at which a vapor-gas mixture must be cooled—at constant humidity—to become saturated. As used herein, "dew point" refers to the temperature at which a water vapor-gas mixture must be cooled—at constant humidity—to become saturated, the gas generally being air.

Figure 3:
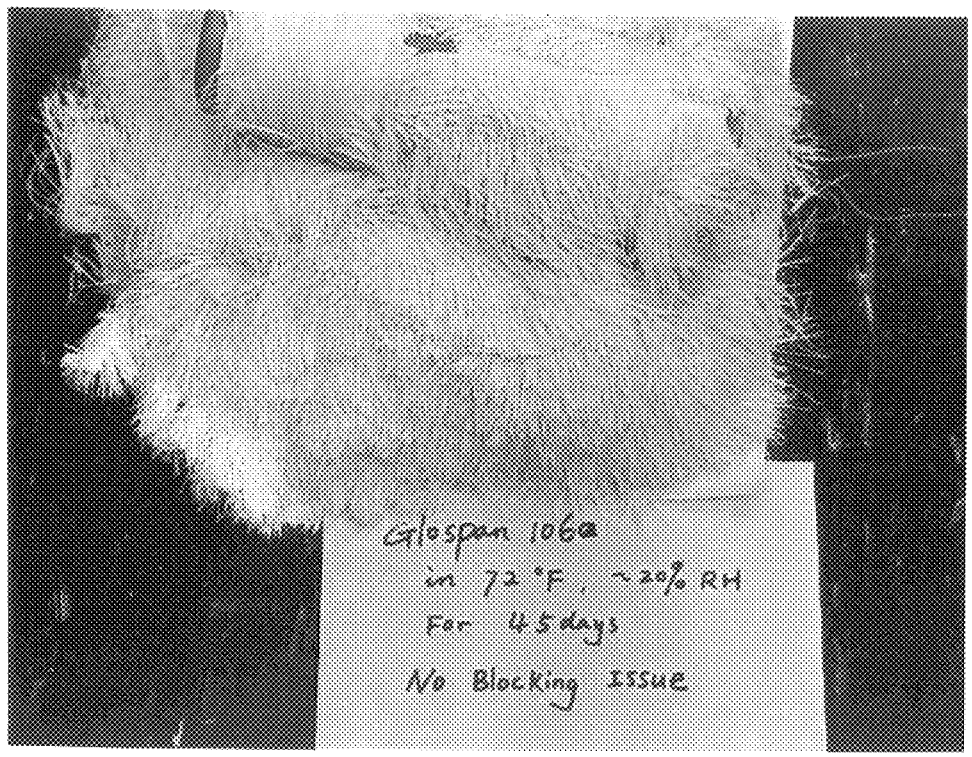
FIG. 3 shows an image of a slit-open spool of strand (specifically, Glospan 1060, which is available from Globe Manufacturing Company, a business having offices in Fall River, Mass.) after the spool had been exposed to a relative humidity of 20% and a temperature of 72° F. for 45 days.

A comparison of two figures gives a visual example of agglomeration behavior. FIG. 3 presents an image of a slit-open spool of GLOSPAN 1060, an elastic material made by Globe Manufacturing Company, a business having offices in Fall River, Mass. GLOSPAN 1060 comprises a polyester-b-polyurethane block copolymer. The strand has cross-sectional dimensions of about 0.2 mm and 1.0 mm, giving a cross-sectional area of about 0.2 $mm^2$. The spool itself comprises a hollow cylinder around which the strand is wound, the cylinder having a radius of 7.5 cm and a length of 28 cm. The strand was wound around the hollow cylinder in a spiral or helical fashion, with the outer surface of the wound-up strand extending radially outwardly from the surface of the hollow cylinder or core a distance of about 3.5 cm from the surface of the cylinder or core. Prior to the spool being slit open, the spool, in its wound-up form, was placed in an environment in which the temperature was 72° F. and the relative humidity was about 20%. A humidity chart for air at atmospheric pressure shows that these conditions correspond to a humidity of about 0.004 pounds-mass ("$lb_m$") of water vapor per $Ib_m$ of dry air. For an example of such a humidity chart, see Warren L. Mcabe and Julian C. Smith, Unit Operations of Chemical Engineering, pg. 748 (3d ed. 1976). After 45 days of exposure to these conditions, the spool, after being slit open, remained substantially unagglomerated.

Figure 7:
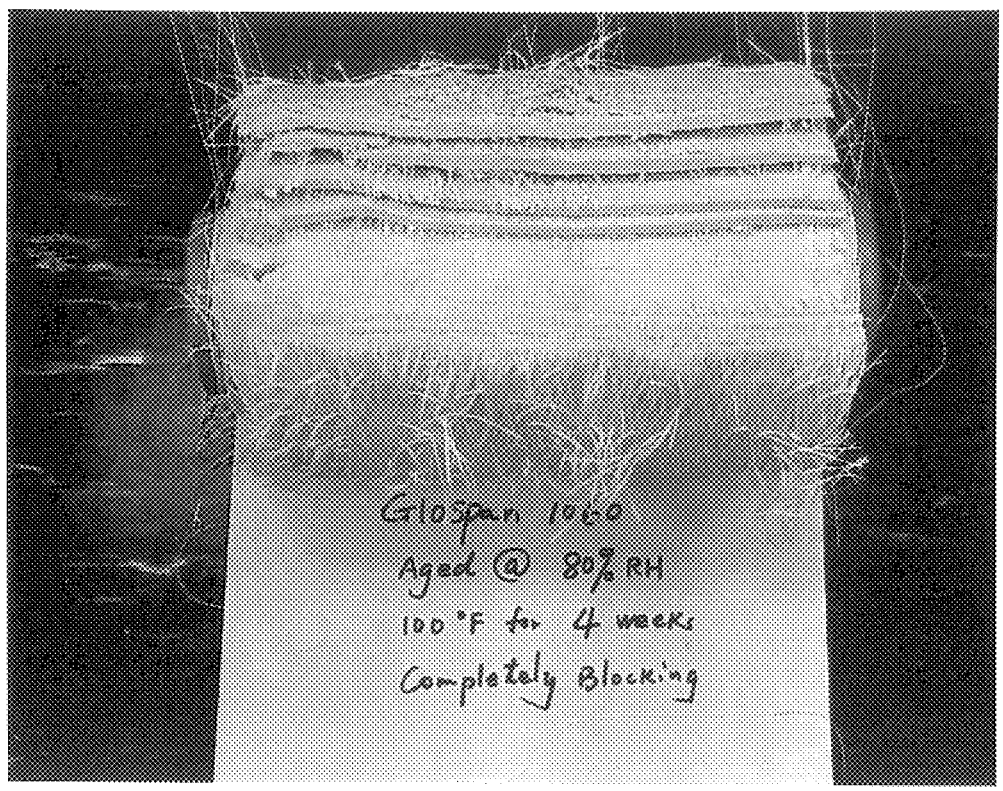
FIG. 7 shows an image of a slit-open spool of strand (specifically, Glospan 1060) after the spool had been exposed to a relative humidity of 80% and a temperature of 100° F. for 4 weeks.

FIG. 7 also presents an image of a slit-open spool of GLOSPAN 1060, but in this case the spool was exposed to a relative humidity of 80%, at a temperature of 100° F., for 35 days. These conditions correspond to a humidity of about 0.034 $lb_m$ of water vapor per $lb_m$ of dry air. As can be seen in this image, segments of the strand have adhered or attached to neighboring segments of the strand such that slab-like agglomerates have formed. If such a spool of agglomerated elastic strand was unwound during production of an article, then a strand segment, when unwound from the spool, would be more likely to break because it might be attached to one or more neighboring segments. The present invention addresses this issue by regulating the amount of water or water vapor experienced by the strand during one or more processing and handling steps occurring after the strand has been extruded, spun, or otherwise made.

In one version of the present invention, one or more of the processing and/or handling steps following extrusion, spinning, or other strand-manufacturing process are conducted in a controlled-humidity environment. This is generally accomplished by carrying out one or more of said steps in a room, compartment, or other enclosure in which a value corresponding to the humidity in the enclosure is controlled so that it does not exceed a selected set point. The set point corresponds to a desired specific humidity or relative humidity. Control generally comprises first sensing or measuring a value corresponding to the specific humidity or relative humidity in the enclosure. Typically, the device used to sense or measure humidity will be in the vicinity of the elastic strand. The sensed or measured value is transmitted to a controller, computer, or other device that compares the sensed or measured value to a set-point value. If the sensed or measured value is different from the set-point value, then a control action may be taken such that the specific humidity or relative humidity in the enclosure is force adjusted to be at or below the desired specific humidity or relative humidity.

Typically, the specific humidity or relative humidity is force adjusted by directing the air/water-vapor mixture across cooling coils so that the temperature of the mixture is reduced below the mixture's dew point. As a result of this cooling process, a portion of the water vapor condenses on the coils and is removed as liquid, thereby reducing humidity. By directing a sufficient amount of the air/water-vapor mixture across the cooling coils, and then conducting the dehumidified air into the enclosure, humidity is force adjusted to the desired level. After water vapor has been condensed and removed by this cooling process, the air may be heated to increase the dry-bulb temperature. As used herein, "dry-bulb temperature" refers to the temperature of the air/water-vapor mixture as indicated by a thermometer placed in the mixture. Accordingly, as used herein, "controlled-humidity" refers to environments in which specific humidity and/or relative humidity are controlled, and, if the air is heated to increase the dry-bulb temperature after the air/water vapor mixture is dehumidified, environments in which the dry-bulb temperature is also controlled or regulated.

The air/water vapor mixture may be taken from inside the enclosure, dehumidified, and then recirculated back to the enclosure; or it may be taken from outside the enclosure, dehumidified, and brought into the enclosure; or both. For example, if an enclosure is built around a winding station to which an elastic strand is continuously directed, there will be an opening in the enclosure to allow the strand to enter and be wound up. If the manufacturing environment is hot and humid, then a slight positive pressure will likely be maintained inside the enclosure to reduce the amount of hot, humid air entering the enclosure through the opening. In this case, some quantity of the air/water vapor mixture outside the enclosure will have to be dehumidified and brought into the enclosure to replace the air/water vapor mixture inside the enclosure that is escaping through the opening because of the positive pressure.

Rather than control humidity so that it is at or below a set-point value, the air inside the room or enclosure can be adjusted to a temperature set point such that the maximum specific humidity cannot exceed a certain level. Humidity charts for air at atmospheric pressure may be used to select the appropriate temperature set point. For example, at a temperature of 40° F., even at a relative humidity of 100%, the specific humidity is about 0.006 $lb_m$ of water vapor per $lb_m$ of dry air. As discussed above, a exposure of elastic material to a specific humidity of about 0.004 $lb_m$ of water vapor per $lb_m$ of dry air for 45 days did not produce significant agglomeration. Accordingly, as used herein, "controlled-humidity temperature" refers to environments in which temperature is controlled to some value in order to regulate the amount of water vapor experienced by the elastic strand.

As stated above, one embodiment of the invention is directed to controlling the humidity of one or more of the processing and/or handling steps following extrusion or spinning. Alternatively, the temperature of the processing and/or handling step(s) may be controlled to limit the capacity of the air to hold water vapor. For example, the step in which the elastic strand is first wound up at a winder may be carried out in a controlled-humidity or controlled-temperature environment. Processing steps upstream or downstream of the first winder may also be carried out in a controlled-humidity or controlled-temperature environment. As used herein, "first winder" refers to the winder at which the strand is first wound up after it is extruded, spun, or otherwise made; "upstream" refers to those processing steps that occur after the strand is extruded or spun, but before the first winder; and "downstream" refers to those processing steps that occur after the first winder. If one or more additional processing steps occur after the first winding step at a separate unwinding/winding station (i.e., a station where the elastic strand is unwound, processed in some way, and rewound), these one or more additional processing steps may be carried out in a controlled-humidity or controlled-temperature environment. To the extent that bobbins of elastic strand are stored prior to use or shipment, the bobbins may be stored in a controlled-humidity or controlled-temperature environment. If elastic strand is being shipped to another location, the step in which the elastic strand is prepared—perhaps involving another step in which the elastic strand is unwound and then wound back up again— and packaged for shipment may also be carried out in a controlled-humidity or controlled-temperature environment. And the step of shipping or transporting the elastic strand itself may be carried out in a controlled-humidity or controlled-temperature environment.

All of these steps—winding, storing, preparing and packaging for shipment (if shipping is necessary), shipping, and perhaps storing again at the location where the strand will be used as a raw material—can be carried out in a controlled-humidity or controlled-temperature environment such that the Agglomeration Index Value does not exceed about 10 grams per strand, particularly about 20 grams per strand, more particularly about 25 grams per strand, and specifically about 30 grams per strand at the time it is used as a raw material on a production machine (e.g., a machine for making a disposable absorbent article).

In some embodiments of the invention, however, one or more of the steps need not be carried out in a controlled-humidity or controlled-temperature environment. For example, the elastic strand can be placed in a container comprising a barrier material. As used herein, "barrier material" refers to a material that is resistant to penetration by water vapor. The step of placing elastic strand in a container comprising a barrier material, e.g. packaging the elastic strand for storage or shipment, may be accomplished in a number of ways. Bobbins of elastic strand, or pallets of bobbins of elastic strand, can be wrapped or encased by a barrier material, e.g. a suitable shrink-wrap. Alternatively, bobbins of elastic strand, or pallets of bobbins of elastic strand, may be placed in a flexible plastic bag comprising a barrier material. Or the elastic strand may be placed in a box or carton comprising a barrier material, e.g. lined with or holding a flexible plastic bag that is resistant to penetration by water vapor. It should be understood that the present invention encompasses other containers comprising a barrier material.

If the elastic strand is placed in a container comprising a barrier material while in a low-humidity environment, then the microenvironment immediately around the elastic strand inside the container will correspond to that low-humidity environment. In another version of the invention, the air/water vapor mixture inside the container may be displaced by a substantially dry gas to create a low-humidity microenvironment around the strand inside the container (see below). Or a desiccant might be added to adsorb/absorb any water vapor inside the container. After the container is closed, subsequent processing steps might be carried out such that the humidity or temperature outside the container is not regulated. The container would likely not be opened until the elastic strand was to be used as a raw material in a production process.

A number of methods may be used to package the elastic strand. The elastic strand may be wound up at a first winder in a controlled-humidity or controlled-temperature environment, and then taken, conducted, or conveyed to a controlled-humidity or controlled-temperature environment for packaging. Alternatively, the elastic strand may be wound up at a first winder and, soon thereafter, taken, conducted, or conveyed to a controlled-humidity or controlled-temperature environment for packaging.

While in a controlled-humidity or controlled-temperature environment, bobbins of elastic strand, or pallets of bobbins of elastic strand are placed in a container comprising a barrier material. Suitable barrier materials that are resistant to penetration by water vapor include, but are not limited to, polyethylene, polypropylene, polyvinyl chloride, polyvinylidene chloride, polyester, polycarbonate, nylon, cellulose, or a combination thereof. The density, thickness, identity, and/or other physical characteristics (e.g., the solubility of water in the selected barrier material) of the barrier material may be selected so that the mass transport of water vapor through the barrier material over the anticipated shipping and/or storage time of the bobbins, spools, or rolls of elastic material will not lead to agglomeration of the material, or will not exceed a selected value. The container is then closed in a way that minimizes the amount of water vapor that might reach the packaged strand during subsequent storage and/or shipping steps. For example, if the container comprising a barrier material is a flexible polyethylene bag or other flexible, water-vapor-resistant plastic bag, then the container can be heat sealed after bobbins of elastic strand, or pallets of bobbins of elastic strand, are inserted into the bag. Alternatively, bobbins of elastic strand, or pallets of bobbins of elastic strand, can be placed in a carton or box lined with a barrier material such as a polyethylene bag, the bag being heat sealed after the bobbins of elastic strand are in place.

In another aspect, a method of the present invention further comprises placing a desiccant material near the elastic strand prior to the container comprising a barrier material being closed, e.g. heat sealed. To the extent that the container allows water vapor to penetrate into and around the elastic strand, the desiccant acts to preferentially adsorb or absorb the water vapor. Accordingly, the desiccant helps to keep the humidity inside the container at a level that minimizes strength degradation.

Examples of useful desiccants include calcium chloride, calcium sulfate, silica gel, a molecular sieve, $Al_2O_3$, and the like. Typically, the desiccant will be put in a receptacle that allows passage of water vapor into the interior of the receptacle and in contact with the desiccant, but keeps the desiccant separate from the elastic strand. An example of a receptacle is a pouch comprising a fibrous web of naturally occurring fibers—typically having cellulose as a primary constituent—or a nonwoven material such as a polyethylene or polypropylene nonwoven fabric. Various physical characteristics of a desiccant (e.g., the mass of water removed per unit mass of desiccant; the residual concentration of water in air after an air/water vapor mixture has been placed in contact with the desiccant under specified conditions) may be evaluated in selecting the type and amount of desiccant to be used. Furthermore, after a barrier material having a specific thickness and density has been selected, one can estimate the amount of water vapor that will diffuse through the barrier material over the anticipated shipping and/or storage time. The type and amount of desiccant may then be selected so that the amount of water vapor that is estimated to penetrate the barrier material will not exceed the capacity of the desiccant to adsorb/absorb the water vapor.

In another aspect, the present invention further comprises the step of displacing the air/water vapor mixture inside the container comprising a barrier material with a dry, inert gas before closing the container. For example, after pallets of bobbins of elastic material have been placed inside a container, dry nitrogen gas may be directed to the interior of the container using a flexible conduit. After sufficient time has passed to allow displacement of the air/water-vapor mixture from inside the container, the conduit is removed from the container, and the container is then closed. This displacement step may be used in conjunction with the step of placing a desiccant material with the elastic material prior to closing the container. The displacement step may or may not be conducted in a controlled-temperature or controlled-humidity environment.

In another aspect, a humidity detector is placed with the elastic strand before the container comprising a barrier material is closed. When the bag or container is opened, most likely after it has been shipped to a purchaser of the elastic strand, the humidity detector can be examined to determine if the humidity inside the container exceeded a certain value. Alternatively, if the bag or container comprising a barrier material is transparent, then the detector could be examined without opening the container. If the humidity did exceed a certain value, then the bag or container could be rejected and sent back to the supplier. Alternatively, a sample from the shipment could be tested immediately. If the strength characteristics of the strand were deemed acceptable, then the shipment could be accepted for use as a raw material. One example of a suitable humidity detector is the humidity indicator corresponding to catalogue number HC-10/60-200, available from Omega Engineering Inc., of Stamford, Conn. The indicator is capable of detecting relative humidity over the range 10 to 60 percent.

The step of placing a humidity detector with the elastic strand may be used in conjunction with: placing a desiccant with the strand before a container comprising a barrier material is closed; displacing the air/water-vapor mixture inside the container comprising a barrier material with a dry, inert gas before closing the container; or both.

In some embodiments of the present invention, bobbins of elastic strand are stored either at the site where the strand is made, at the site where the strand is used as a raw material, or both. If the strand is unpackaged during these storage steps, and the strand is to be stored for more than 10, specifically more than 20, and particularly more than 30 days, then the room, facility, or area in which the strand is stored may be a controlled-humidity or controlled-temperature environment. But, as discussed above, all of the process and handling steps subsequent to the strand being extruded or spun may be carried out in controlled-humidity or controlled-temperature environment—regardless of the total time between extrusion or spinning of the strand and use of the strand as a raw material—to minimize or eliminate strength degradation. Or the elastic strand can be packaged so that the "micro-environment" inside the container comprising a barrier material has a low water-vapor content (i.e., a low humidity), thereby allowing subsequent processing steps to be carried out such that the environment outside the package need not be controlled.

Elastic strands processed or handled in accordance with the present invention may be incorporated into a number of substrate composites and disposable absorbent articles. Examples of such substrate composites and/or disposable absorbent articles are described in U.S. Pat. No. 4,940,464, entitled "Disposable Incontinence Garment or Training Pant," which is hereby incorporated by reference in its entirety; U.S. Pat. No. 5,904,675, entitled "Absorbent Article with Improved Elastic Margins and Containment System," which is hereby incorporated by reference in its entirety, with column 7, lines 7 through 34 discussing use of elastic strands with a containment flap, and column 9, line 29 through column 10, line 36 discussing elastic members; U.S. Pat. No. 5,904,672, entitled "Absorbent Article having Improved Waist Region Dryness and Method of Manufacture," which is hereby incorporated by reference in its entirety, with column 11, line 39 through column 12, line 2 discussing elastic leg members; and U.S. Pat. No. 5,902,297, entitled "Absorbent Article Having a Collection Conduit," which is hereby incorporated by reference in its entirety. It should be understood that the present invention is applicable to other structures, composites, or products incorporating one or more elastic strands.

An example of a method and apparatus for making an elastomeric laminate web (i.e., for purposes of the present application, a substrate composite incorporating elastic strand) which may be used with the present invention is found in U.S. Pat. No. 5,964,973, entitled "Method and Apparatus for Making an Elastomeric Laminate Web," which is hereby incorporated by reference in a manner consistent with the present specification. Again it should be understood that this patent gives exemplars of methods and apparatuses for incorporating elastic strands into substrate composites, and the present invention may be used with other methods and apparatuses used to make substrate composites.

Tests

Agglomeration Index Value

Agglomeration Index Value is measured in the following manner. First, a roll of strand, typically comprising strand wound around a core, is obtained. The core generally is cylindrical with an axial dimension and a radial dimension. The strand is slit or cut with a razor, knife, or other cutting instrument such that the slit or cut is parallel to the axial dimension of the core. The depth of the slit or cut may equal the distance from the outer surface of the roll of strand to the outer surface of the core around which the strand is wound up, or some increment thereof. FIG. 3 displays an image of a roll in which the roll of elastic strand, after being cut in the axial dimension, unraveled in the form of substantially unagglomerated strand segments. FIG. 7 displays an image of a roll in which the roll of elastic strand, after being cut in the axial dimension, unraveled in the form of agglomerated strand segments (e.g., slab-like agglomerates in which one strand segment is attached to one or more neighboring strand segments).

If the rolled-up strand, after being slit, unravels in the form of substantially unagglomerated strand, then the Agglomeration Index Value is not measured (the measurement would prove difficult if an individual strand did not adhere to any of its neighbors). Instead the Agglomeration Index Value is equated to zero. If, however, the rolled-up strand, after being slit, unravels in the form of agglomerated strand, then the core and agglomerated strand are placed on a support proximate to a tensile-testing device. For our measurements, a Sintech tensile tester having model number 3108-128, available from MTS System Corporation, a business having offices in Eden Prairie, Minn., was used. The tensile tester was modified by attaching an alligator clamp to a length of wire. The wire was then attached to the tensile tester such that tester was capable of operably measuring the load, in grams, required to pull 1 or 2 strand segments from the strand agglomerate, with the strand segment(s) secured by the closed alligator clamp (see FIGS. 13.A., 13.B., 13.C., and 13.D.).

The slit-open roll of strand is placed on the support such that the cut(s) or slit(s) in the rolled-up strand is opposite the clamp used to pull a predetermined number of strand segments away from the strand agglomerate (for our experiments, 1 or 2 strand segments; see FIGS. 13.A., 13.B., 13.C., and 13.D.). When manipulating the clamp so that a predetermined number of segments are fastened by the clamp prior to starting the test, the clamp is manipulated so as to minimize initial separation between the strand segment(s) to be pulled away from neighboring strand segments. The tester is then activated so that the clamp is drawn away from the surface of the slit-open strand material. The clamp is drawn away in a direction that is substantially perpendicular to the surface of the slit-open strand material, and at a speed of 300 mm/min. As the alligator clamp is drawn away from the surface of the strand agglomerate by the action of the tensile tester, the 1 or 2 strands that are fastened by the closed alligator clamp are pulled away, and detached, from the strand agglomerate. The tensile tester measures the load, in grams, required to pull the predetermined number of strand segments from neighboring strand segments. The Agglomeration Index Value corresponds to the average of five to ten replicates of this test, with load measured as the peak load that occurs during the test (i.e., the maximum load detected during the course of the test). If two strands are used when conducting the test, then the peak load (in grams) is divided by two to give dimensions of grams per strand.

In some cases, the Agglomeration Index Value was determined for strand located at a position proximate to: the surface of the wound-up spool of strand; the surface of the core around which the strand was wound ("core position"); and/or a region approximately half way between the surface of the core and the surface of the spool of strand ("middle position"). The Agglomeration Index Value of strand at the middle- and core-positions was measured by cutting or slicing the wound-up spool and peeling off strands, or layers of strand, until a strand (or strands) at the desired testing position was exposed for completing the test as outlined above. Also, as shown in FIG. 13.C., an object may be inserted into the core around which the elastic strand is wound if the pulling of strand(s) away from the strand agglomerate would move the core (typically this doesn't occur.)

Although the present invention has been described in considerable detail with reference to certain versions, other versions are possible. The spirit and scope of the appended claims should not be limited to the description of specific versions contained herein.

EXAMPLES

Example 1

A bobbin or spoof of GLOSPAN 1060, an elastic strand comprising a polyester-b-polyurethane block copolymer, was obtained from Globe Manufacturing Company. The number "1060" corresponds to the denier of the strand; i.e. about 1060 denier or about 1060 grams per 9000 meters of strand. The elastic strand had been coated with a lubricant. As received, the strand was wound up around a hollow core. The core had a radius of 7.5 cm (radial dimension) and a length of 28 cm (axial dimension). The strand was wound around the core to form a tube comprising the helically- or spirally-wound strand. The outer surface of the tube of strand extended radially outwardly from the surface of the core at a distance of about 3.8 cm from the surface of the core. The length of the tube of helically- or spirally-wound strand was about the same as the length of the core. (Note: the strand might be systematically accumulated to form shapes other than a tube or cylinder comprising the individual strand or strands.) The individual strand had a cross-sectional area of about 0.2 mm$^2$ (calculated by multiplying the cross-sectional dimensions of the strand: 1.0 mm multiplied by 0.2 mm).

Figure 4:
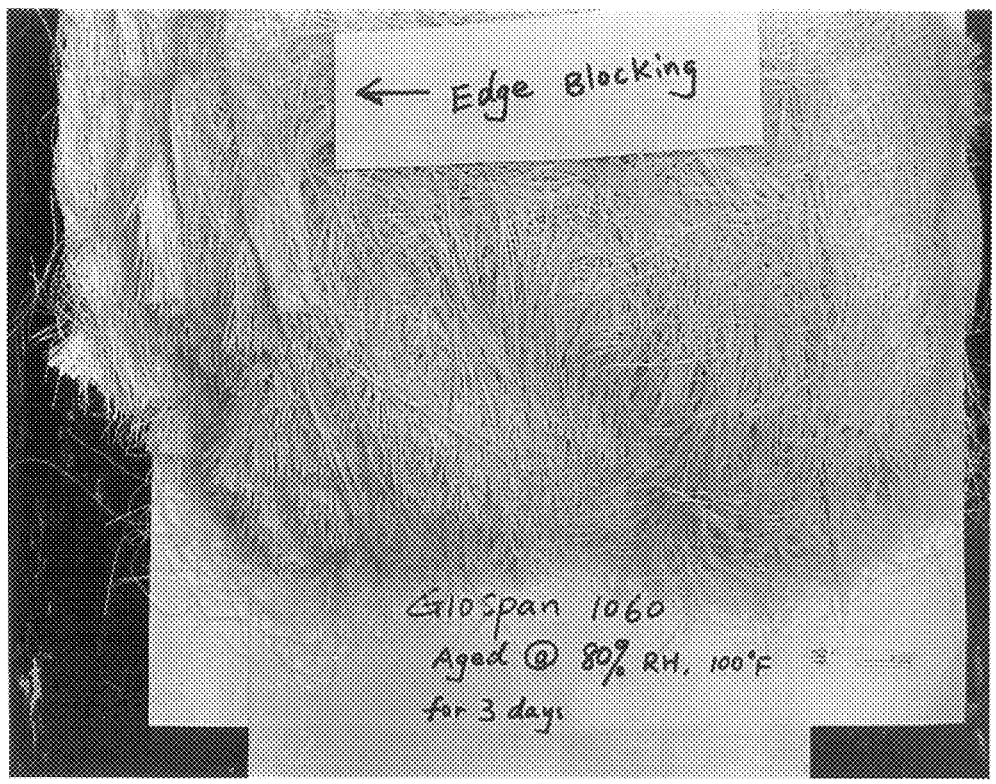
FIG. 4 shows an image of a slit-open spool of strand (specifically, Glospan 1060) after the spool had been exposed to a relative humidity of 80% and a temperature of 100° F. for 3 days.

When received from the manufacturer, the spool comprised substantially unagglomerated strand. Spools of Glospan 1060 were placed in a controlled environment, with the temperature controlled to a value of about 100° F. and the relative humidity controlled to a value of about 80%. The spools were exposed to these conditions for various times: 3 days, 5 days, 2 weeks, 4 weeks, and 35 days. After each of these conditioning times had elapsed, a spool was taken to a room having a temperature of about 72–75° F. and a relative humidity of about 50%. The spool was then systematically slit along its length with a razor blade. Typically, the spool was slit within 30 minutes after the spool was removed from the environment having a temperature of about 100° F. and a relative humidity of about 80%. Generally, the blade was inserted so that the edge of the blade penetrated to a depth of about 0.5 to 1 cm or so from the surface of the spool. The razor was then drawn along the axial dimension of the spool from one end of the spool to the other. This slitting process was repeated, generally until a position proximate to the core was reached. Depending on the time of exposure to the temperature of about 100° F. and the relative humidity of about 80%, the roll of strand exhibited different degrees of agglomeration. After 3 days of exposure, a majority of the roll remained substantially unagglomerated, but the edge of the roll appeared to show some agglomeration (see FIG. 4; agglomeration of the strand at the edge is denoted as "edge blocking" in the figure). Similar behavior was seen after 5 days of exposure (see FIG. 5; agglomeration of the strand at the edge is denoted as "edge blocking" in the figure; "open to air" indicates that exposure to the prevailing conditions—a temperature of about 100° F. and the relative humidity of about 80%—was not regulated; unless otherwise specified, spools of elastic material were placed in conditioning environments so that the material was exposed to the prevailing conditions). After 2 weeks of exposure to a temperature of about 100° F. and a relative humidity of about 80%, a spool of Glospan 1060 that had been systematically slit down shows that agglomeration had increased, with slab-like structures resulting from the slitting process. (see FIG. 6). In other words, systematically cutting the spool produced a peeled-onion-like structure comprising layered slabs of agglomerated strand. Spools of Glospan 1060 exposed to a temperature of about 100° F. and the relative humidity of about 80% for 4 weeks and 35 days again showed agglomeration throughout the roll of strand. (see FIGS. 7 and 8, respectively). The sequence of images depicted in FIGS. 4, 5, 6, 7, and 8 establish that exposure to certain conditions causes a roll of elastic material to agglomerate (i.e., strand segments begin to adhere to a least some portion of neighboring strand segments).

Example 2

A bobbin or spool of GLOSPAN 770, an elastic strand comprising a polyester-b-polyurethane block copolymer, was obtained from Globe Manufacturing Company. The number "770" corresponds to the denier of the strand; i.e. about 770 denier or about 770 grams per 9000 meters of strand. The elastic strand had been coated with a lubricant. The strand was wound up around a hollow core. The core had a radius of 7.5 cm (radial dimension) and a length of 28 cm (axial dimension). The strand was wound around the core to form a tube comprising the helically- or spirally-wound strand. The outer surface of the tube of strand extended radially outwardly from the surface of the core at a distance of about 3.5 cm from the surface of the core. The length of the tube of helically- or spirally-wound strand was about the same as the length of the core. (Note: the strand might be systematically accumulated to form shapes other than a tube or cylinder comprising the individual strand or strands.) The individual strand had a cross-sectional area of about 0.1 mm$^2$ (calculated by multiplying the cross-sectional dimensions of the strand: 0.2 mm multiplied by 0.5 mm).

Figure 11:
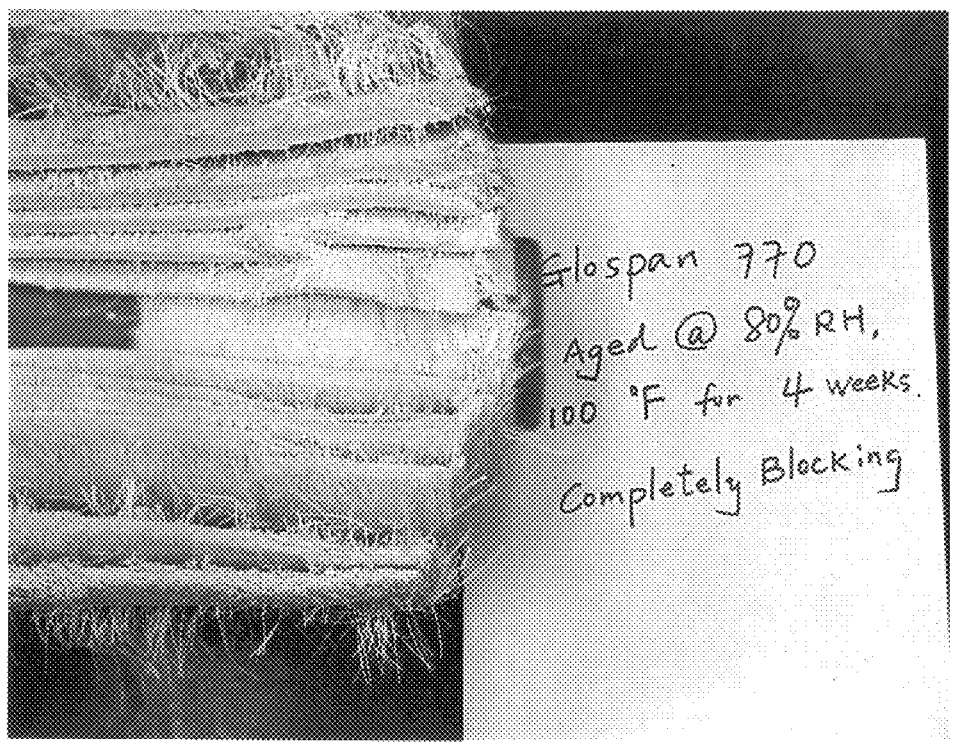
FIG. 11 shows an image of a slit-open spool of strand (specifically, Glospan 770, which is available from Globe Manufacturing Company, a business having offices in Fall River, Mass.) after the spool had been exposed to a relative humidity of 80% and a temperature of 100° F. for four weeks.

When received from the manufacturer, the spool comprised substantially unagglomerated strand. The spool of Glospan 770 was placed in a controlled environment, with the temperature controlled to a value of 100° F. and the relative humidity controlled to a value of 80%. After the spool was exposed to these conditions for 4 weeks, it was removed from the environment. The spool was then taken to a room having a temperature of about 72–75° F. and a relative humidity of about 50%. The spool was then systematically slit along its length with a razor blade. Typically, the spool was slit within about 30 minutes after the spool was removed from the environment having a temperature of about 100° F. and a relative humidity of about 80%. The blade was inserted so that the edge of the blade penetrated to a depth of about 0.5 to 1 cm or so from the surface of the spool. The razor blade was then drawn along the axial dimension of the spool from one end of the spool to the other. As depicted in FIG. 11, slitting the spool of strand in this fashion produced a first slab of agglomerated strand (this first slab is located farthest from the core). Repeated slits made in a similar fashion produced additional slabs of agglomerated strand. Systematically cutting the spool in this way produced a peeled-onion-like structure comprising layered slabs of agglomerated strand. Thus, a four-week exposure to a temperature of 100° F. and a relative humidity of 80% caused the strand to agglomerate.

Example 3

A bobbin or spool of GLOSPAN 1120, an elastic strand comprising a polyester-b-polyurethane block copolymer, was obtained from Globe Manufacturing Company. The number "1120" corresponds to the denier of the strand; i.e. about 1120 denier or about 1120 grams per 9000 meters of strand. The elastic strand had been coated with a lubricant. The strand was wound up around a hollow core. The core had a radius of 8 cm (radial dimension) and a length of 11 cm (axial dimension). The strand was wound around the core to form a tube comprising the helically- or spirally-wound strand. The outer surface of the tube of strand extended radially outwardly from the surface of the core at a distance of about 6 cm from the surface of the core. The width of the tube of helically- or spirally-wound strand was about 7.5 cm. (Note: the strand might be systematically accumulated to form shapes other than a tube or cylinder comprising the individual strand or strands.) The individual strand had a cross-sectional area of about 0.22 mm$^2$ (calculated by multiplying the cross-sectional dimensions of the strand: 0.22 mm multiplied by 1.0 mm).

When received from the manufacturer, the spool comprised substantially unagglomerated strand. The spool of Glospan 1120 was placed in a controlled environment, with the temperature controlled to a value of 100° F. and the relative humidity controlled to a value of 80%. After the spool was exposed to these conditions for 15 days, it was removed from the environment. The spool was then taken to a room having a temperature of about 72–75° F. and a relative humidity of about 50%. The spool was then systematically slit along its length with a razor blade. Typically, the spool was slit within about 30 minutes after the spool was removed from the environment having a temperature of about 100° F. and a relative humidity of about 80%. The blade was inserted so that the edge of the blade penetrated to a depth of about 0.5 to 1 cm or so from the surface of the spool. The razor blade was then drawn along the axial dimension of the spool from one end of the spool to the other. As depicted in FIGS. 12.A. and 12.B., slitting the spool of strand in this fashion produced a first slab of agglomerated strand (this first slab is located farthest from the core). Repeated slits made in a similar fashion produced additional slabs of agglomerated strand. Systematically cutting the spool in this way produced a peeled-onion-like structure comprising layered slabs of agglomerated strand. Thus a fifteen-day exposure to a temperature of 100° F. and a relative humidity of 80% caused the strand to agglomerate.

Example 4

The process outlined in Example 1 for systematically slitting a spool of strand was carried out on another spool of Glospan 1060. In this case, the spool of Glospan 1060 was placed in an environment having a temperature of about 72° F. and a relative humidity of about 20%. The spool of Glospan 1060 was removed from this environment after 45 days of exposure to these conditions and slit down as described in Example 1. As shown in FIG. 3, slitting the spool of Glospan 1060 in this manner unraveled the spool to produce substantially unagglomerated strand. Thus exposure to a lesser amount of water or water vapor reduced or eliminated agglomeration of the strand.

Example 5

Spools of GLOSPAN 770 and GLOSPAN 1060 were obtained from the Globe Manufacturing Company. The elastic strand had been coated with a lubricant for each of these bobbins. The approximate dimensions of the core, the tube of helically- or spirally-wound strand surrounding the tube, and the cross-sectional area of an individual strand are given in the above examples for GLOSPAN 1060 and GLOSPAN 770.

When received from the manufacturer, each of the spools comprised substantially unagglomerated strand. One spool of Glospan 770 and two spools of Glospan 1060 were both placed in a controlled environment, with the temperature controlled to a value of about 100° F. and the relative humidity controlled to a value of about 80%. After 2 weeks of exposure to these conditions, one spool of GLOSPAN 1060 was removed from the controlled environment. Using the Agglomeration-Index-Value test described above, the Agglomeration Index Value was determined for strand proximate to two locations: the surface of the spool of strand; and surface of the core. After 2 months of exposure to these conditions, the remaining spool of GLOSPAN 1060 and the remaining spool of GLOSPAN 770 were both removed from the controlled environment. Using the Agglomeration-Index-Value test described above, the Agglomeration Index Value was determined for strand proximate to two locations for GLOSPAN 1060: the surface of each spool of strand; and the surface of each core. The Agglomeration Index Value was determined at three locations for GLOSPAN 770, as discussed below.

Table 1 presents results for GLOSPAN 1060.

TABLE 1

Measurement of blocking force between Glospan 1060 strands aged @ 80% RH, 100° F.
(By Sintech, 300 mm/min, 75° F.)

| Sample | Aging time | Strand position | Blocking/peak load (gm) | Note |
| --- | --- | --- | --- | --- |
| Fresh Glospan | 0 | Surface | 0 | Strand falls from roll, no blocking |
| Fresh Glospan | 0 | Core | 0 | No blocking |
| Aged Glospan | 2 weeks | Surface | 30 | Blocking |
|  | 2 weeks | Core | 76 | Blocking |
| Aged Glospan | 2 months | Surface | 43.5 | Blocking |
|  | 2 months | Core | 133 | Blocking |

Glospan 1060 denoted as "fresh" (i.e., examined and tested as received from the manufacturer without the spools of strand being placed in a controlled environment having a temperature of 100° F. and a relative humidity of 80%) did not exhibit agglomeration (i.e., did not exhibit "blocking"). When a spool of "fresh" GLOSPAN 1060 was systematically slit down as described above, the strand unraveled in the form of substantially unagglomerated strands. Accordingly, the Agglomeration Index Value (i.e., the peak-load value measured using the Agglomeration-Index-Value test described above) was equated to 0.

After exposure to a temperature of 100° F. and a relative humidity of 80% for two weeks, a spool of GLOSPAN 1060 exhibited agglomeration behavior at locations proximate to the surface of the tube of strand and the surface of the core. Furthermore, the Agglomeration Index Value at these locations was determined to be 30 and 76 grams per strand, respectively (with the Agglomeration Index Value denoted as "Blocking/Peak Load" in Table 1).

After exposure to a temperature of 100° F. and a relative humidity of 80% for two months, a spool of GLOSPAN 1060 exhibited agglomeration behavior at locations proximate to the surface of the tube of strand and the surface of the core. Furthermore, the Agglomeration Index Value at these locations was determined to be 43.5 and 133 grams per strand, respectively.

The spool of GLOSPAN 770 exposed to a temperature of 100° F. and a relative humidity of 80% for two months exhibited agglomeration behavior at locations proximate to the surface of the tube of strand, the region half way between the surface of the tube of strand and the surface of the core, and the surface of the core. Furthermore, the Agglomeration Index Value at these locations was determined to be 24.5, 42.5, and 71 grams per strand, respectively.

The data show that continued exposure to water or water vapor causes strands or strand segments to attach or adhere to neighboring strands or strand segments, thus forming agglomerated strand that requires additional force to pull apart.

Example 6

Spools of GLOSPAN 1060 were obtained from the Globe Manufacturing Company. The elastic strand had been coated with lubricant for each of these bobbins. The approximate dimensions of the core, the tube of helically- or spirally-wound strand surrounding the tube, and the cross-sectional area of an individual strand are given in the above examples for GLOSPAN 1060.

When received from the manufacturer, each of the spools comprised substantially unagglomerated strand. Eight spools of Glospan 1060 were placed in a controlled environment, with the temperature controlled to a value of about 100° F. and the relative humidity controlled to a value of about 80%. Four of the spools were placed in the controlled environment so that they were exposed to the prevailing conditions. Four of the spools were first prepared in accordance with one version of the invention in order to regulate exposure of the strand to water or water vapor. Before these four spools were put in the controlled environment, each spool was placed in a polyethylene bag having dimensions of 60 cm by 30 cm by 10 cm and a thickness of 4 mils (i.e., 0.0004 inches). After a spool was placed in the bag, 100 grams of a drying agent, in this case $CaSO_4$, was placed in the bag. In this experiment, the drying agent was first placed in a nonwoven polypropylene receptacle, and the polypropylene receptacle containing the drying agent was then placed in the polyethylene bag containing the spool. A dry nitrogen gas (purity of gas was 99.99% nitrogen) was then conducted to the interior of the bag. This was done by connecting one end of a piece of tubing to a cylinder of nitrogen gas, positioning the other end of the tubing inside the bag, and opening the valve on the cylinder. After approximately 5 minutes, the tubing was withdrawn from inside of the bag and the bag was heat sealed using heat-sealing equipment. The room in which these four spools were sealed in polyethylene bags containing a drying agent had a temperature of about 72–75° F. and a relative humidity of about 50%. After four spools were prepared in accordance with one version of the invention, they too were placed in the controlled environment having temperature controlled to a value of about 100° F. and the relative humidity controlled to a value of about 80%.

After about 5 days (114 hours), a spool of Glospan 1060 that had been open to the conditioned environment and a spool of Glospan 1060 that had been sealed in a polyethylene bag with desiccant were removed from the controlled environment. Each of these spools was systematically slit down as described in the above Examples. Furthermore, the mechanical properties of strand segments were measured at locations proximate to the surface of the tube of wound-up strand, the region half way between the surface of the tube of strand and the surface of the core, and the surface of the core. Furthermore, observations were made regarding the degree of agglomeration (described as "blocking" in the table) that had occurred. This process was repeated at about 234 hours (approximately 10 days), 14 days, and 35 days. The results of these measurements are presented in Table 2 (see next page).

TABLE 2

Effect of aging on mechanical properties of Glospan 1060
Aging @ 80% RH, 100° F. for different times
(Rolls of Glospan 1060 were aged. The samples were taken from surface, middle and core of the roll then tested.)
(T.S. = tensile strength, peak load gm; Elong. % = elongation @ break %

| | Strand from surface | | Strand from middle | | Strand from core | | |
|---|---|---|---|---|---|---|---|
| Sample | T.S. gm | Elong. % | T.S. gm | Elong. % | T.S. gm | Elong. % | Note |
| Aging 114 hr | | | | | | | |
| Open to air | 535 | 1043 | 591 | 1250 | 597 | 1226 | Edge blocking |
| *sealed/dry | 586 | 1273 | 616 | 1408 | 605 | 1380 | No discoloration of $CaSO_4$ |
| Aging 234 hr | | | | | | | |
| Open to air | 416 | 977 | 444 | 1116 | 493 | 1084 | Some blocking |
| *sealed/dry | 600 | 1239 | 596 | 1181 | 604 | 1260 | ~20% of $CaSO_4$ discolored; no blocking |
| Aging 14 days | | | | | | | |
| Open to air | 475 | 998 | 493 | 1091 | 515 | 1142 | Some blocking |
| *sealed/dry | 638 | 1144 | 616 | 1232 | 606 | 1217 | Discoloration of $CaSO_4$; no blocking |
| Aging 35 days | | | | | | | |
| Open to air | 420 | 997 | 425 | 972 | 474 | 1024 | Blocking |
| *sealed bag | 574 | 1114 | 576 | 1324 | 562 | 1271 | Most $CaSO_4$ discolored after 20 days; no blocking |

*SEALED/DRY = Roll of Glospan 1060 was put in polyethylene bag with 100 gm dry agent and sealed under $N_2$.

Co-pending U.S. patent application Ser. No. 60/166348 (Attorney Docket No. 15,427) is entitled "Method for Regulating Strength Degradation in an Elastic Strand," and was filed on Nov. 19, 1999. This co-pending application is hereby incorporated by reference in a manner consistent herewith. The co-pending application is generally directed to a method and apparatus for regulating exposure of an elastic strand to water or water vapor, thereby regulating degradation of strength characteristics of the strand due to the action of water vapor or water on the strand. The results in Table 2 of the present application demonstrate that strength degrades due to the action of water vapor. For spools of Glospan 1060 left open to the prevailing conditions in the controlled environment (i.e., about 80% relative humidity at a temperature of about 100° F.), tensile strength (as represented by the peak-load value, in grams, corresponding to the load at which the strand failed) generally decreases with time of exposure to the prevailing conditions. For spools of Glospan 1060 that had been sealed in polyethylene bags with a drying agent, any strength decrease that may have occurred was less than that for the spools of Glospan 1060 that had been left open to the prevailing conditions in the controlled environment (as indicated in Table 2, the drying agent became discolored indicating that the drying agent may have been close to saturation, thereby decreasing its ability to adsorb water). Thus the peak-load values (i.e., tensile strength) of elastic material sealed in polyethylene bags with a desiccant were significantly higher than for elastic material that was exposed to the conditions prevailing in the controlled environment (i.e., about 80% relative humidity at a temperature of about 100° F.).

Figure 5:
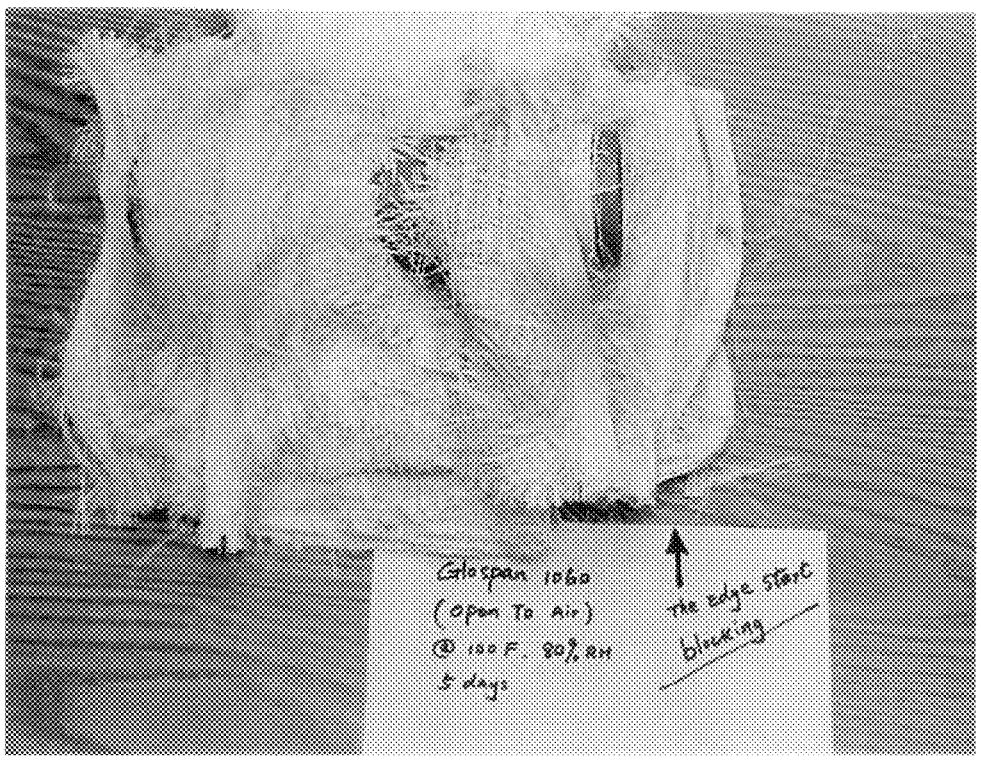
FIG. 5 shows an image of a slit-open spool of strand (specifically, Glospan 1060) after the spool had been exposed to a relative humidity of 80% and a temperature of 100° F. for 5 days.
Figure 6:
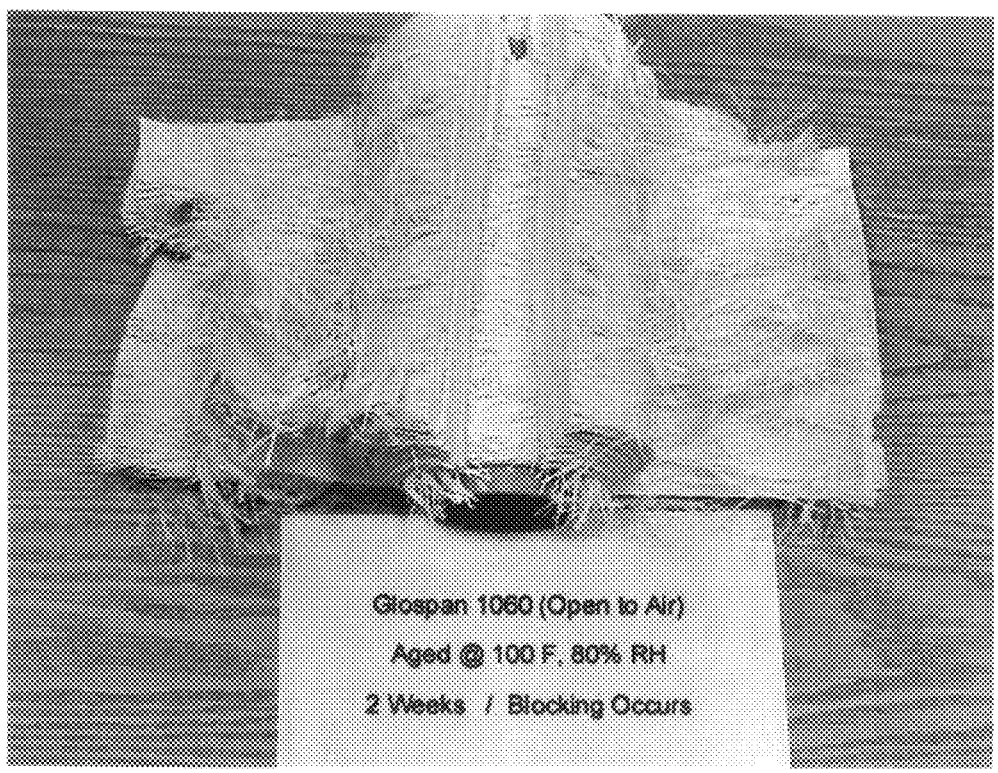
FIG. 6 shows an image of a slit-open spool of strand (specifically, Glospan 1060) after the spool had been exposed to a relative humidity of 80% and a temperature of 100° F. for 2 weeks.
Figure 8:
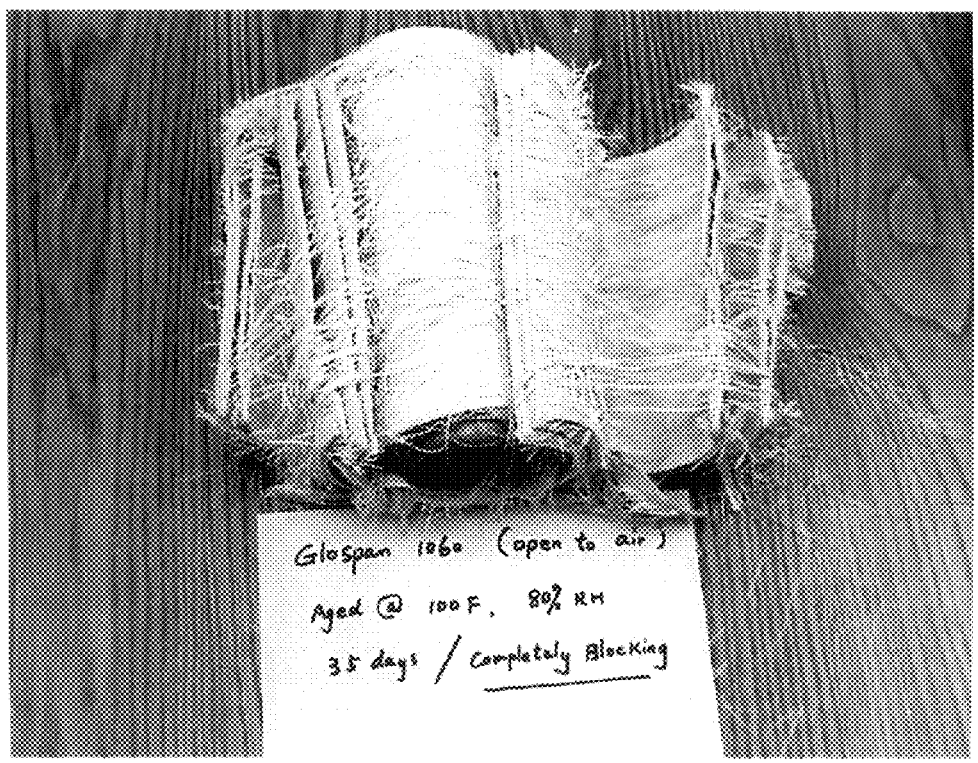
FIG. 8 shows an image of a slit-open spool of strand (specifically, Glospan 1060) after the spool had been exposed to a relative humidity of 80% and a temperature of 100° F. for 35 days.
Figure 9:
FIG. 9 shows an image of a slit-open spool of strand (specifically, Glospan 1060) after the spool, which had been placed in a bag with 100 g of $CaSO_4$ and sealed after the air/water mixture inside the bag had been displaced by substantially dry nitrogen gas, had been exposed to a relative humidity of 80% and a temperature of 100° F. for two weeks.

Furthermore, sealing spools of Glospan 1060 in polyethylene bags with a drying agent significantly decreased agglomeration. As shown in FIGS. 5, 6, and 8 (these images correspond to the spools from which individual strand segments were removed for determining the mechanical properties presented in Table 2 ), those spools of Glospan 1060 left open to conditions prevailing in the controlled environment became agglomerated (or "blocked"). Those spools that were sealed in polyethylene bags with a drying agent, however, experienced significantly less agglomeration. For example, the slit-down spool depicted in FIG. 9 shows a spool of Glospan 1060 that had been sealed in a polyethylene bag with 100 grams of $CaSO_4$ before being placed in a controlled environment having a temperature of about 100° F. and a relative humidity of about 80% for two weeks. The figure shows that the strand is substantially unagglomerated. FIG. 6, on the other hand, depicts a slit-down spool of Glospan 1060 that had been left open to the conditions prevailing in the controlled environment for two weeks. Slab-like agglomerates of strand have formed.

Figure 10:
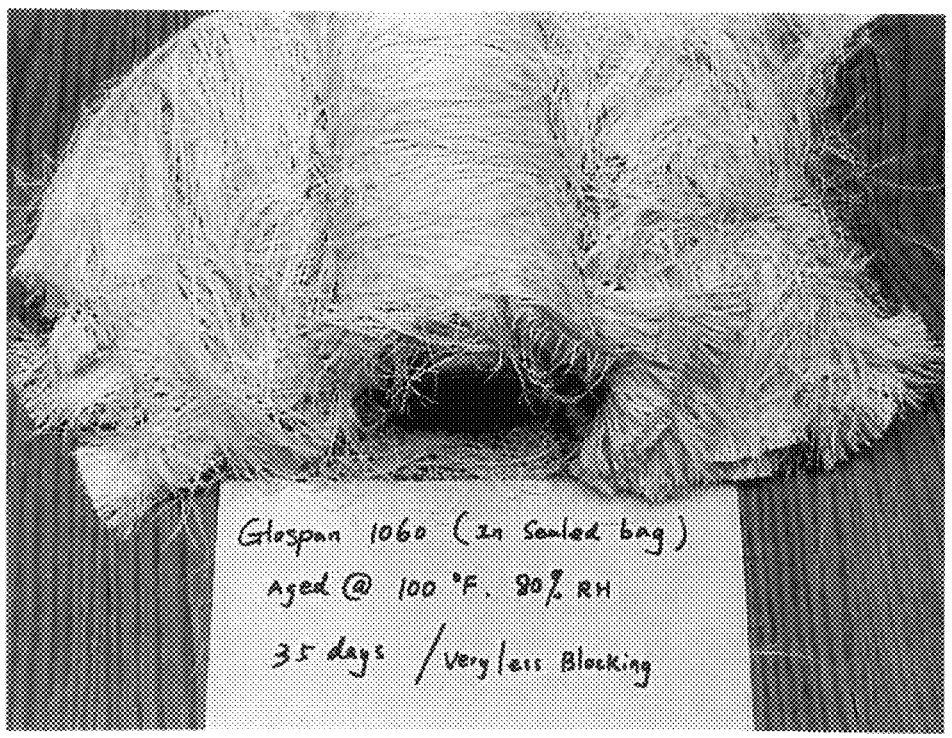
FIG. 10 shows an image of a slit-open spool of strand (specifically, Glospan 1060) after the spool, which had been placed in a bag with 100 g of $CaSO_4$ and sealed after the air/water mixture inside the bag had been displaced by substantially dry nitrogen gas, had been exposed to a relative humidity of 80% and a temperature of 100° F. for 35 days.

A similar comparison is found at 35 days. Glospan 1060 left exposed to the conditions prevailing in the controlled environment experienced significant agglomeration (see FIG. 8). Glospan 1060 , sealed in a polyethylene bag with 100 grams of $CaSO_4$ experienced little, if any agglomeration (see FIG. 10).

Example 7

A bobbin or spool of LYCRA 940, an elastic strand comprising a polyether-b-polyurethane block copolymer, was obtained from Dupont Corp., a business having offices in Wilmington, Del. The number "940" corresponds to the decitex of the strand. The strand was wound up around a hollow core. The core had a radius of 7.5 cm (radial dimension) and a length of 8.5 cm (axial dimension). The strand was wound around the core to form a tube comprising the helically- or spirally-wound strand. The outer surface of the tube of strand extended radially outwardly from the surface of the core at a distance of about 9 cm from the surface of the core. The length of the tube of helically- or spirally-wound strand was about the same as the length of the core. (Note: the strand might be systematically accumulated to form shapes other than a tube or cylinder comprising the individual strand or strands.) The individual strand had a cross-sectional area of about 0.2 $mm^2$ (calculated by multiplying the cross-sectional dimensions of the strand: 0.2 mm multiplied by 1.0 mm).

As received the spool of LYCRA 940 had some agglomeration. A slit-down spool had a peeled-onion-like structure of slabs of agglomerated strand. The Agglomeration Index Values were determined to be 19.5, 40, and 35 grams per strand at locations proximate to the surface of the tube of strand, the region half way between the surface of the tube of strand and the surface of the core, and the surface of the core.

A spool was then placed in a controlled environment at a temperature of about 100° F. and a relative humidity of about 80%. The spool was left exposed to the conditions prevailing in the controlled environment. After the spool had been exposed to these conditions for 1 month, the spool was removed and Agglomeration Index Values determined. The Agglomeration Index Values were determined to be 27, 53, and 67 grams per strand at locations proximate to the surface of the tube of strand, the region half way between the surface of the tube of strand and the surface of the core, and the surface of the core. Thus, exposure to these conditions resulted in an increase in the degree of adherence between neighboring strand segments in the spool of LYCRA 940. Furthermore, exposure to these conditions resulted in an decrease of the average peak-load value from about 740 grams to about 660 grams.

What is claimed is:

1. A method of handling substantially unagglomerated elastic strand so that the strand remains substantially unagglomerated, the method comprising the steps of:

providing substantially unagglomerated, elastic strand; and regulating exposure of the strand to water or water vapor so that the strand remains substantially unagglomerated.

2. The method of claim 1 wherein the strand's exposure to water or water vapor is regulated such that the specific humidity around the strand does not exceed about 0.01 pounds-mass of water vapor per pound-mass of dry air during storage of the strand at the geographic site where the strand is made, shipping of the strand between the geographic site where the strand is made and the geographic site where the strand is to be used as a raw material, storage of the strand at the geographic site where the strand is to be used as a raw material, or some combination thereof.

3. The method of claim 2 wherein the strand is used as a raw material to produce a substrate composite comprising the strand or an absorbent article comprising the strand.

4. The method of claim 3 wherein the specific humidity around the strand does not exceed about 0.005 pounds-mass of water vapor per pound-mass of dry air.

5. The method of claim 3 wherein the strand's exposure to water vapor is regulated during shipping of the strand between the geographic site where the strand is made and the geographic site where the strand is used as a raw material.

6. The method of claim 5 wherein regulating the strand's exposure to water vapor comprises controlling the temperature around the strand or around a container that contains the strand.

7. The method of claim 6 wherein the temperature is controlled to a value not exceeding about 55 degrees Fahrenheit.

8. The method of claim 5 wherein regulating the strand's exposure to water vapor comprises controlling the humidity around the strand or around a container that contains the strand.

9. The method of claim 7 or 8 wherein the strand comprises polyester, polyurethane, polyether, polyamide, polyacrylate, polyester-b-polyurethane block copolymer, polyether-b-polyurethane block copolymer, or polyether-b-polyamide block copolymer.

10. The method of claim 8 wherein the strand's exposure to water vapor is regulated such that the Agglomeration Index Value of the strand at the time the strand is used as a raw material to produce a substrate composite comprising the strand, or an absorbent article comprising the strand, is less than about 20 grams per strand.

11. The method of claim 8 wherein the strand's exposure to water vapor is regulated such that the Agglomeration Index Value of the strand at the time the strand is used as a raw material to produce a substrate composite comprising the strand, or an absorbent article comprising the elastic strand, is substantially zero.

12. The method of claim 1 wherein regulating the strand's exposure to water or water vapor comprises the steps:

placing the strand in a container comprising a barrier material resistant to penetration by water vapor; and closing the container comprising the barrier material.

13. The method of claim 12 wherein the container comprising the barrier material is closed at a time $t_1$, time $t_1$ being after the time when the strand is first produced and before the time when the strand is shipped from the geographical site where the strand is made to the geographical site where the strand is used as a raw material.

14. The method of claim 13 wherein the specific humidity around the strand does not exceed 0.017 pounds-mass of water vapor per pound-mass of dry air between time $t_1$ and time $t_2$, time $t_2$ being the time when the closed container comprising a barrier material is first opened.

15. The method of claim 13 wherein the specific humidity around the strand does not exceed 0.01 pounds-mass of water vapor per pound-mass of dry air between time $t_1$ and time $t_2$, time $t_2$ being the time when the closed container comprising a barrier material is first opened.

16. The method of claim 13 wherein the specific humidity around the strand does not exceed 0.005 pounds-mass of water vapor per pound-mass of dry air between time $t_1$ and time $t_2$, time $t_2$ being the time when the closed container comprising a barrier material is first opened.

17. The method of claim 14 wherein the barrier material is polyethylene, polypropylene, polyvinyl chloride, polyvinylidene chloride, polyester, polycarbonate, nylon, cellulose, or some combination thereof.

18. The method of claim 17 wherein closing the container comprising a barrier material comprises heat sealing the container, the barrier material, or both.

19. The method of claim 14 further comprising the step of placing desiccant material with the strand before closing the container comprising the barrier material.

20. The method of claim 19 wherein the desiccant material comprises calcium chloride, calcium sulfate, silica gel, a molecular sieve, $Al_{23}$, or some combination of these.

21. The method of claim 18 or 20 further comprising the steps of displacing any mixture of air and water vapor from the interior of the container comprising a barrier material with an inert dry gas before heat sealing the container, barrier material, or both; placing a humidity indicator inside the container comprising a barrier material before heat sealing the container, barrier material, or both; or both.

22. The method of claims 17 wherein the elastic strand comprises polyester, polyurethane, polyether, polyamide, polyacrylate, polyester-b-polyurethane block copolymer, polyether-b-polyurethane block copolymer, or polyether-b-polyamide block copolymer.

23. The method of claim 14 wherein the strand's exposure to water vapor is regulated such that the Agglomeration Index Value of the strand at the time the strand is used as a raw material to produce a substrate composite comprising the strand, or an absorbent article comprising the strand, is less than about 20 grams per strand.

24. The method of claim 14 wherein the strand's exposure to water vapor is regulated such that the Agglomeration Index Value of the strand at the time the strand is used as a raw material to produce a substrate composite comprising the strand, or an absorbent article comprising the elastic strand, is substantially zero.

25. The method of claim 23 or 24 wherein the tensile strength of the strand at the time the strand is used as a raw material to produce a substrate composite comprising the strand, or an absorbent article comprising the strand, has not decreased by more than about 20% from the tensile strength of the strand when the strand was first produced.

* * * * *